(12) United States Patent
Brady et al.

(10) Patent No.: US 8,168,431 B2
(45) Date of Patent: *May 1, 2012

(54) TISSUE ENGINEERING SCAFFOLD COMPRISING POLYURETHANE MATERIAL HAVING VOIDS INTERCONNECTED BY PORES

(75) Inventors: Eamon Brady, Elphin (IE); Ann Marie Cannon, Pettigo (IE); Fergal Farrell, Athy (IE); Gerard McCaffrey, Galway (IE)

(73) Assignee: Cellology Limited, Galway (IE)

( * ) Notice: Subject to any disclaimer, the term of this patent is extended or adjusted under 35 U.S.C. 154(b) by 560 days.

This patent is subject to a terminal disclaimer.

(21) Appl. No.: 12/271,336

(22) Filed: Nov. 14, 2008

(65) Prior Publication Data

US 2009/0163612 A1   Jun. 25, 2009

Related U.S. Application Data

(63) Continuation of application No. 11/152,780, filed on Jun. 15, 2005, now abandoned, which is a continuation of application No. 09/985,822, filed on Nov. 6, 2001, now abandoned, which is a continuation of application No. PCT/IE00/00059, filed on May 8, 2000.

(30) Foreign Application Priority Data

May 7, 1999  (WO) .................... PCT/IE99/00037
May 7, 1999  (WO) .................... PCT/IE99/00038

(51) Int. Cl.
C12N 5/07     (2010.01)
C12N 11/08    (2006.01)
A61F 2/00     (2006.01)
C08G 18/00    (2006.01)
C08G 64/00    (2006.01)

(52) U.S. Cl. ........ 435/396; 424/423; 435/180; 525/452; 528/196

(58) Field of Classification Search .................... None
See application file for complete search history.

(56) References Cited

U.S. PATENT DOCUMENTS

| | | |
|---|---|---|
| 4,186,448 A | 2/1980 | Brekke |
| 4,687,482 A | 8/1987 | Hanson |
| 5,478,867 A | 12/1995 | Tabor |
| 5,856,367 A | 1/1999 | Barrows et al. |
| 5,993,972 A | 11/1999 | Reich et al. |
| 6,147,168 A | 11/2000 | Jamiolkowski et al. |
| 6,177,522 B1 | 1/2001 | Brady et al. |
| 6,187,329 B1 | 2/2001 | Agrawal et al. |
| 6,379,962 B1 | 4/2002 | Holy et al. |

Primary Examiner — David Naff
(74) Attorney, Agent, or Firm — Sughrue Mion, PLLC; Jonathan Feuchtwang

(57) ABSTRACT

A tissue engineering scaffold for cell, tissue or organ growth comprises a biocompatible porous polyurethane cellular material comprising a plurality of substantially spherical voids of diameter from 20 to 300 microns, preferably 80 to 200 microns, interconnected by generally elliptically shaped pores. The cellular material has a void content of from 85% to 98% and a surface area to volume of from 5 to 400 $mm^2/mm^3$, ideally from 20 to 80 $mm^2/mm^3$.

46 Claims, 17 Drawing Sheets

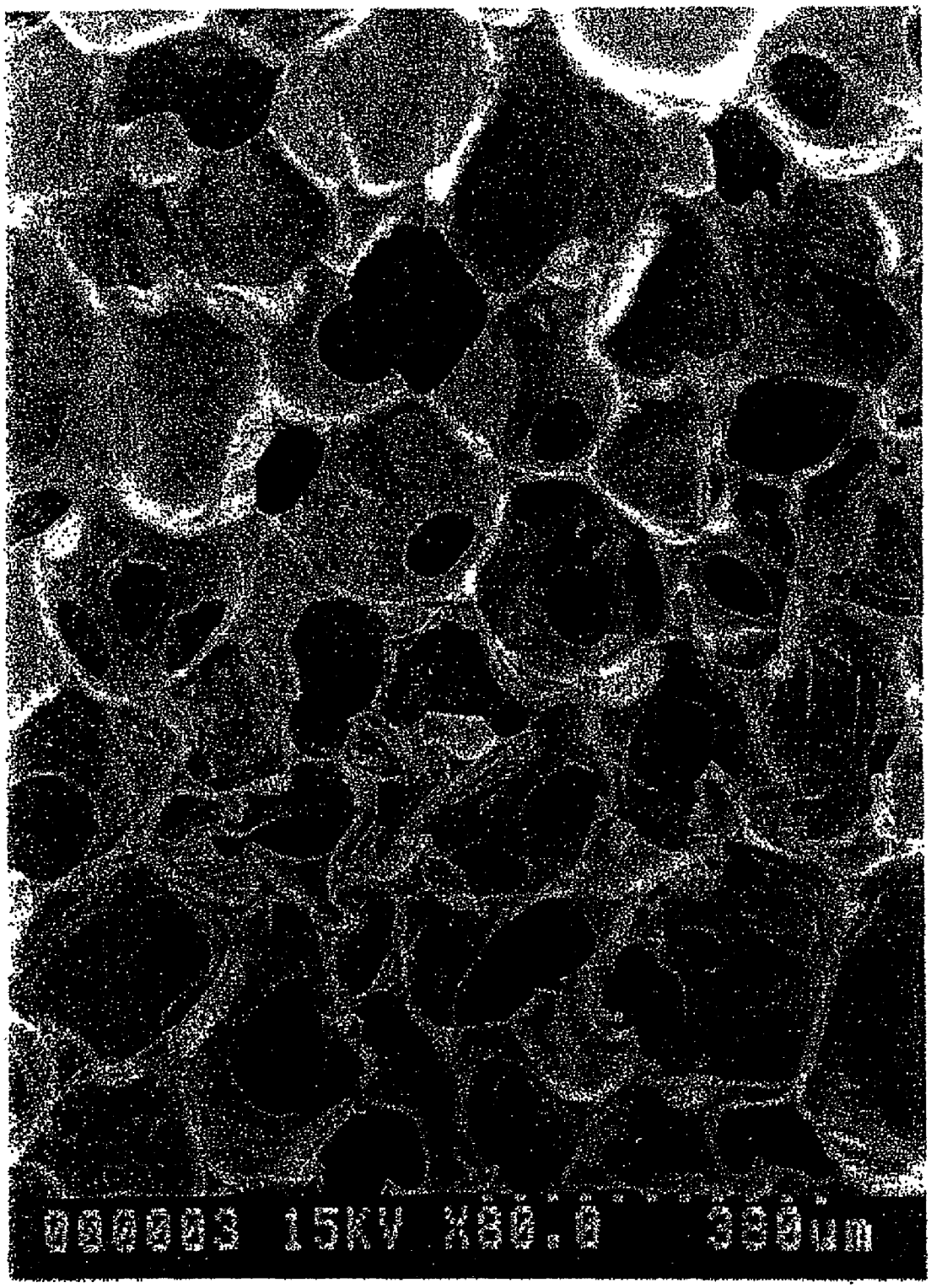
Fig. 1.0

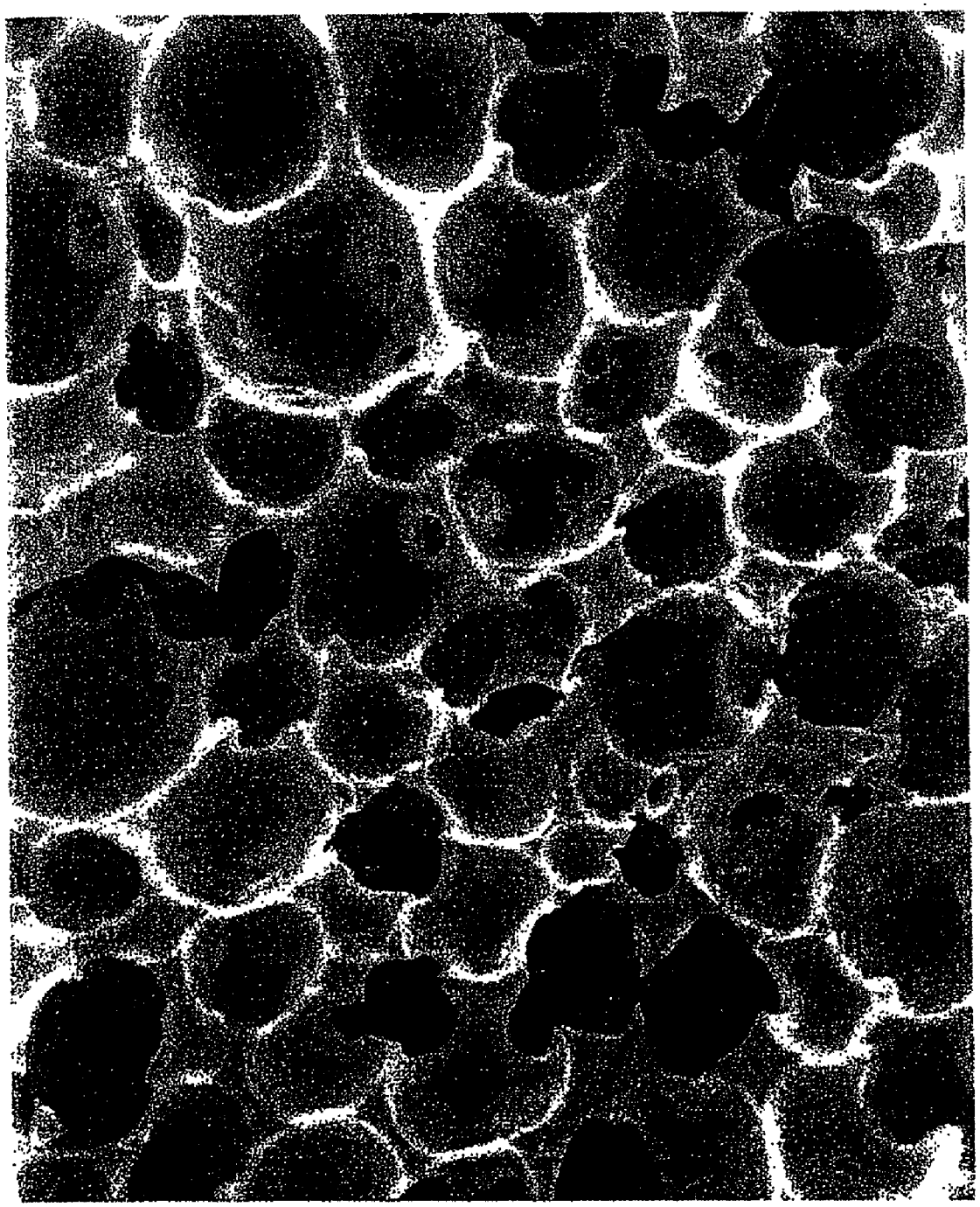
Fig. 1.1

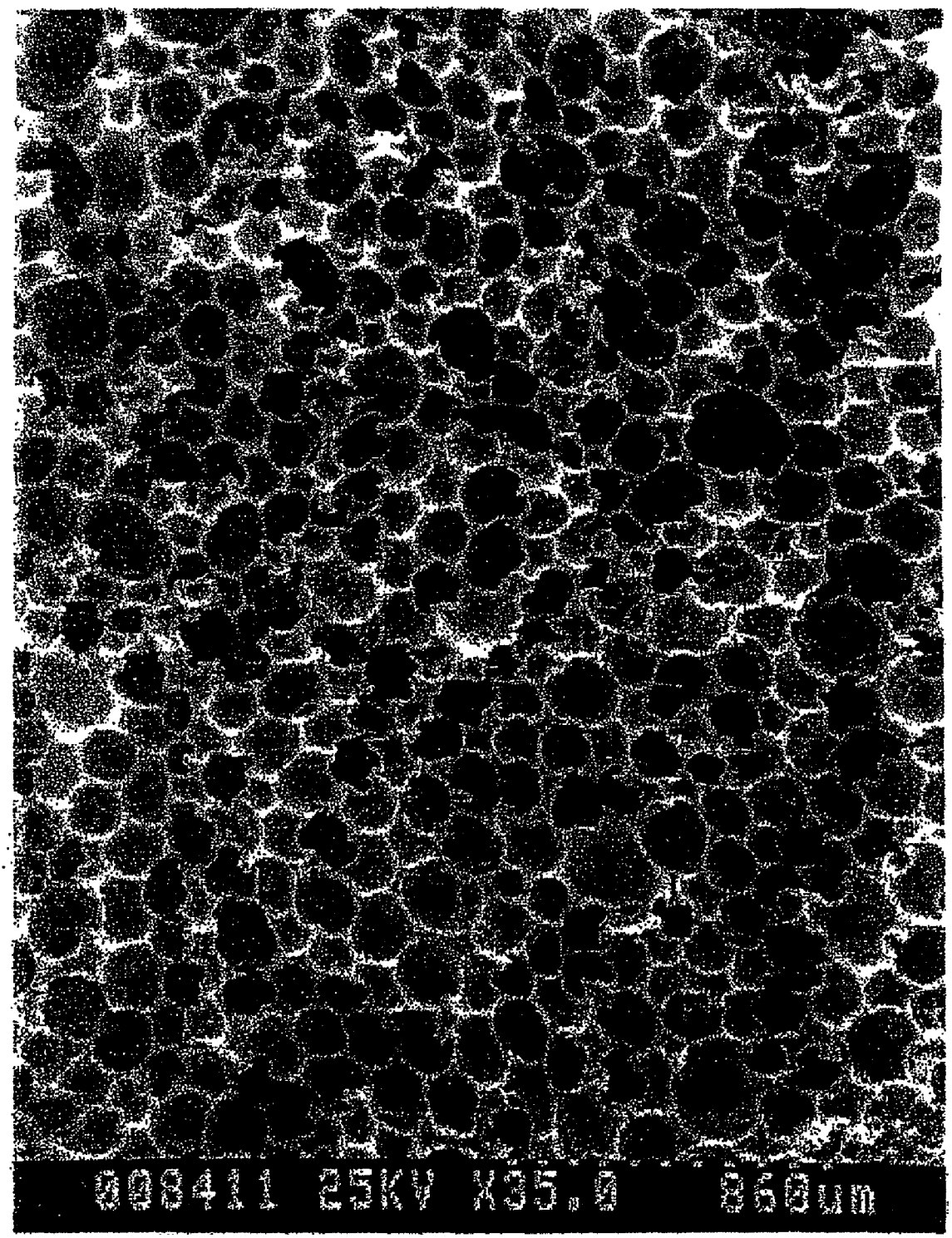
Fig. 1.2

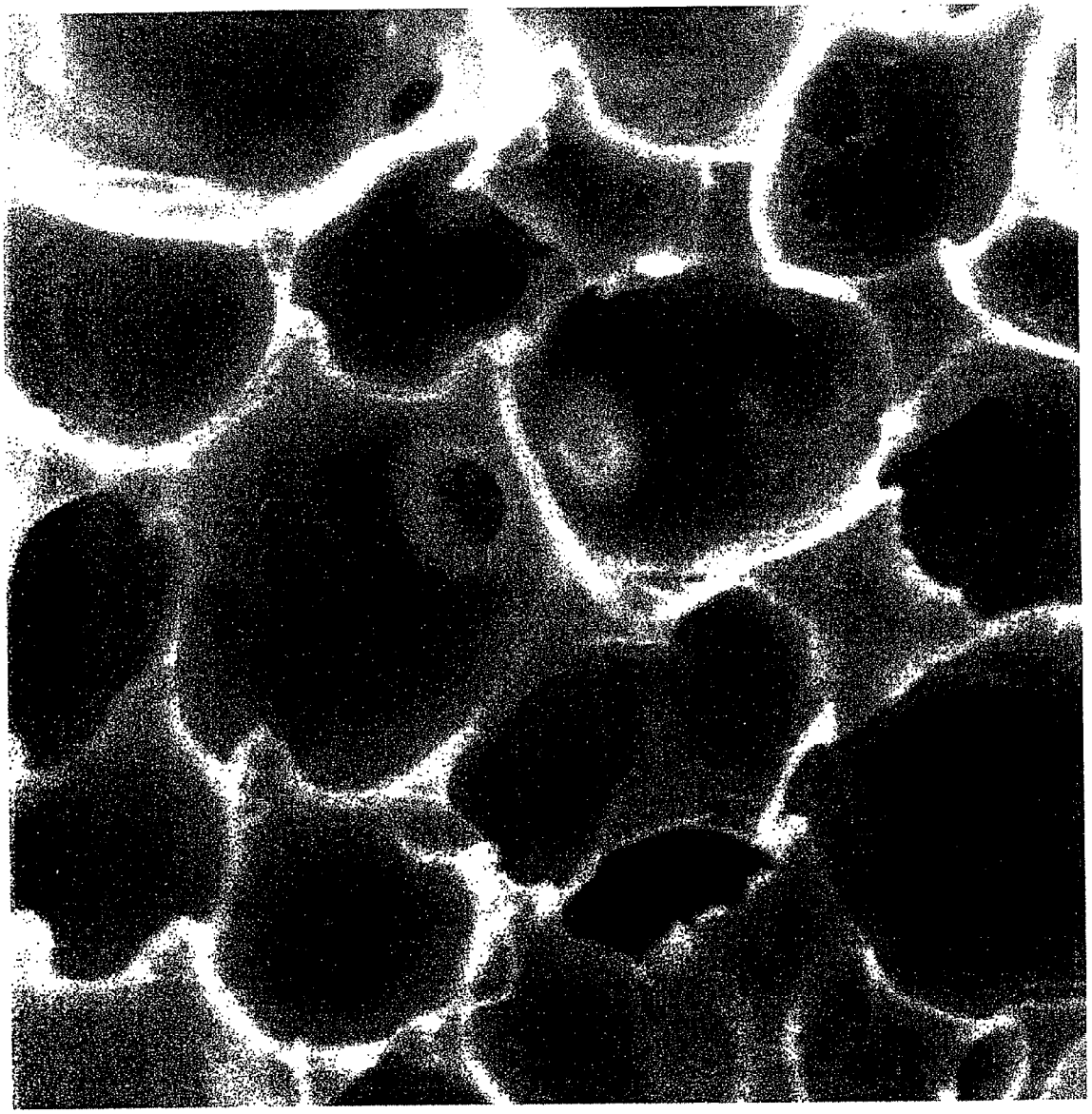
Fig. 1.3

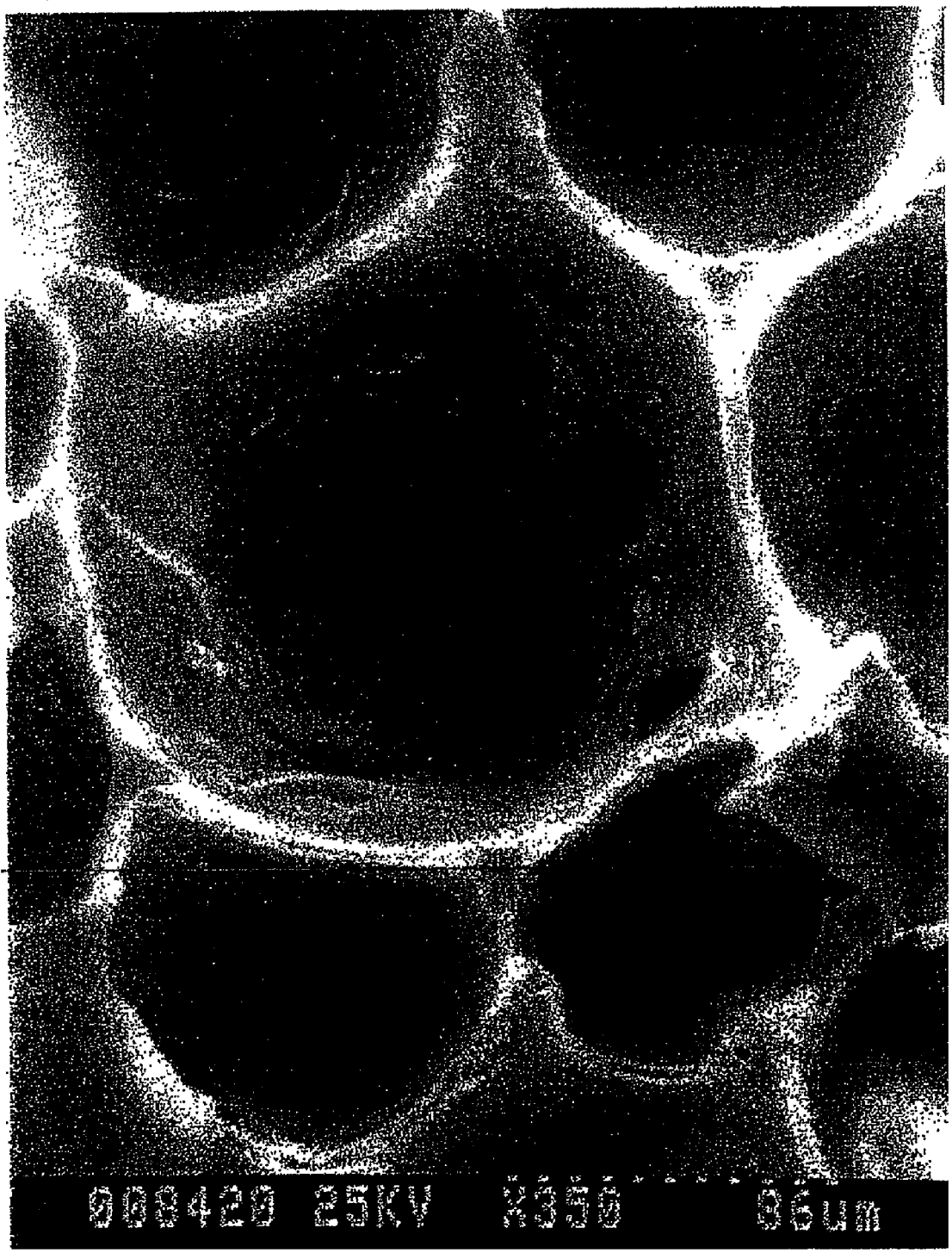
Fig. 1.4

Fig. 1.5

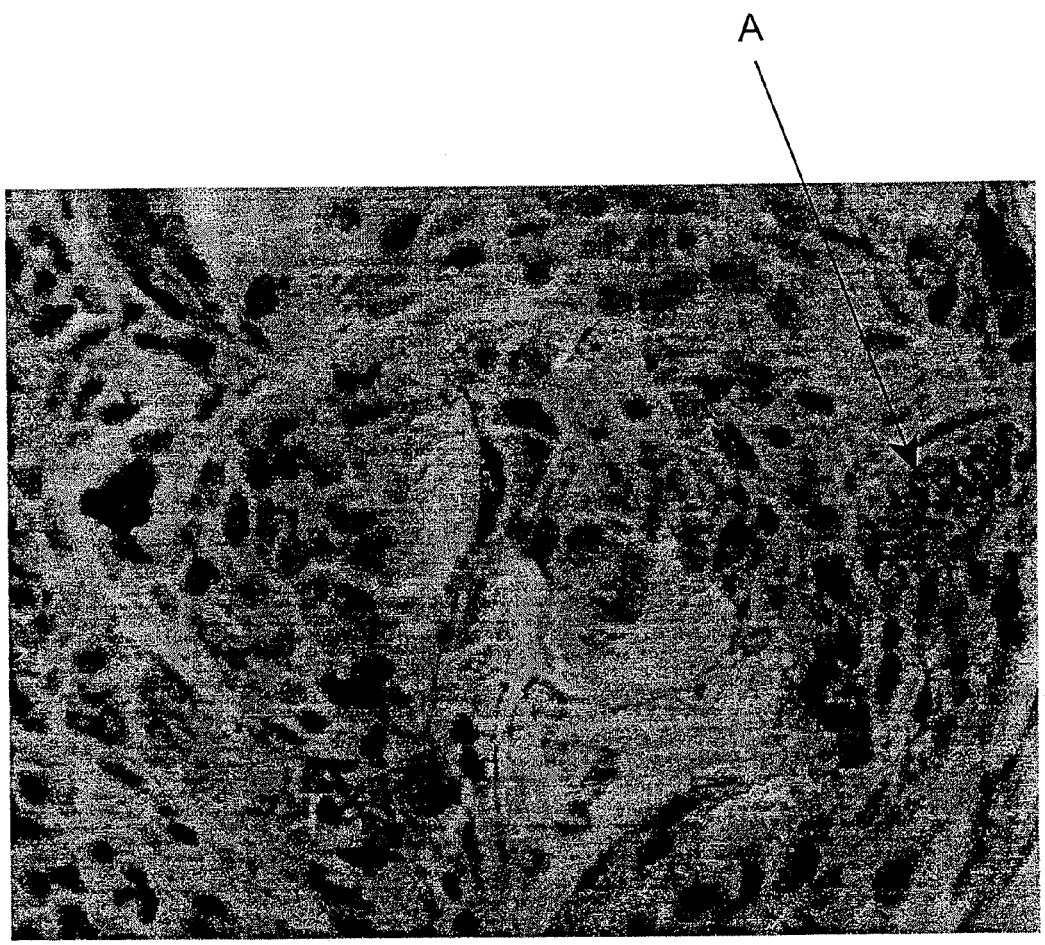
Fig. 2.1

Fig 2.2

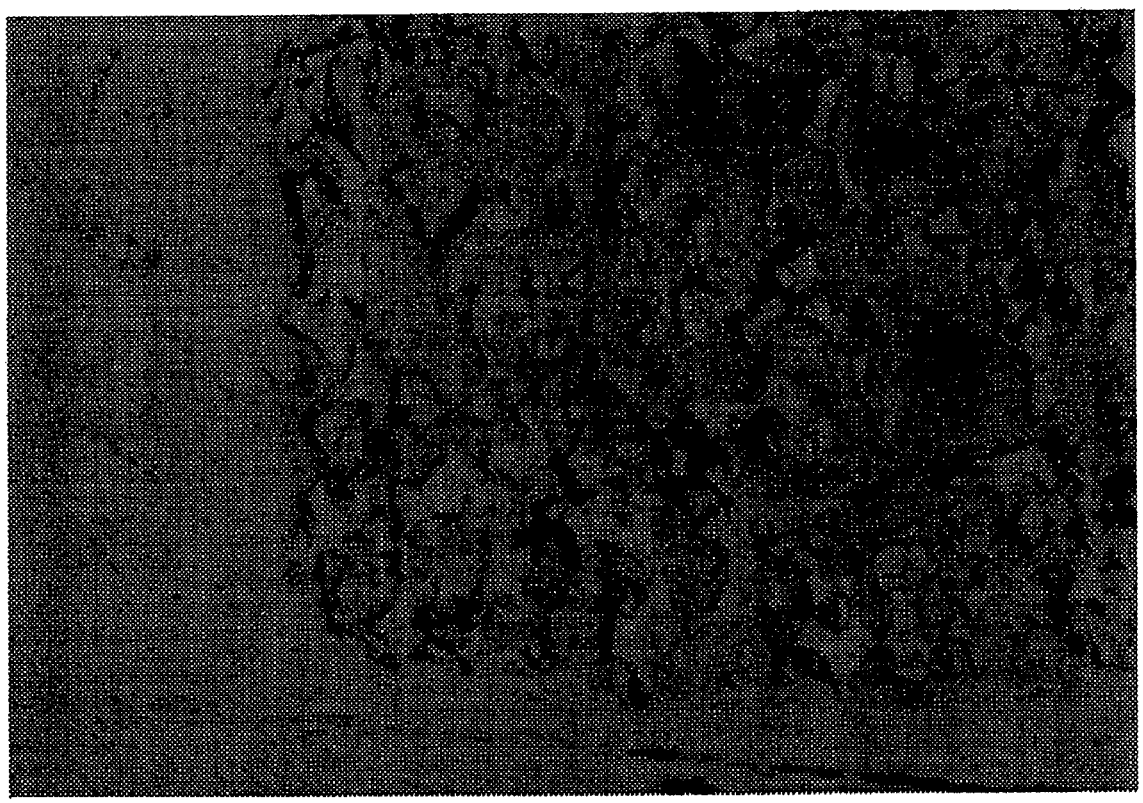
Fig. 2.3

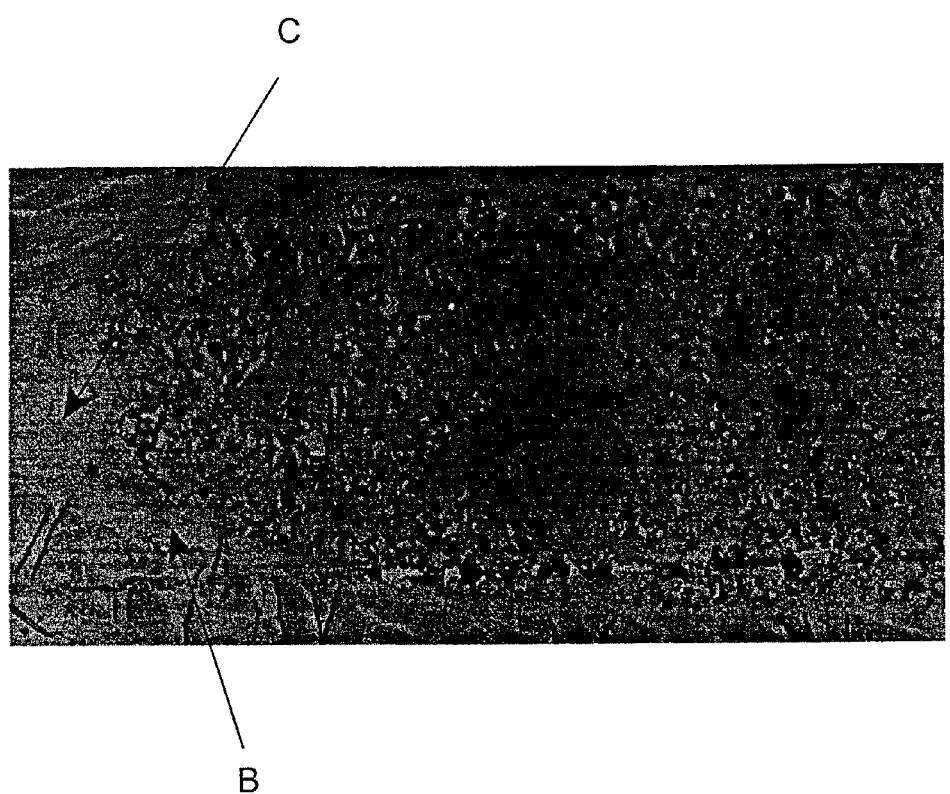
Fig. 2.4

Fig. 2.5A
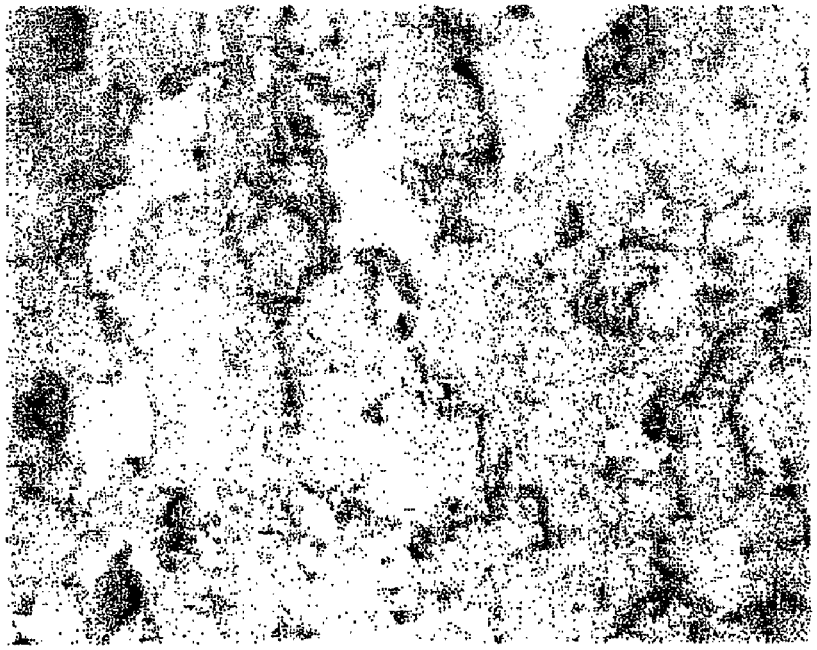
Fig. 2.5B
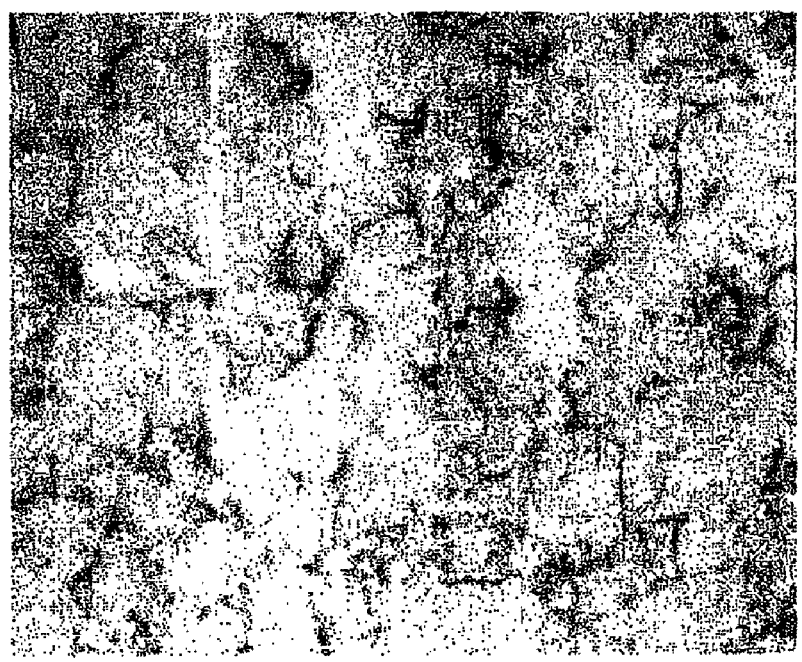

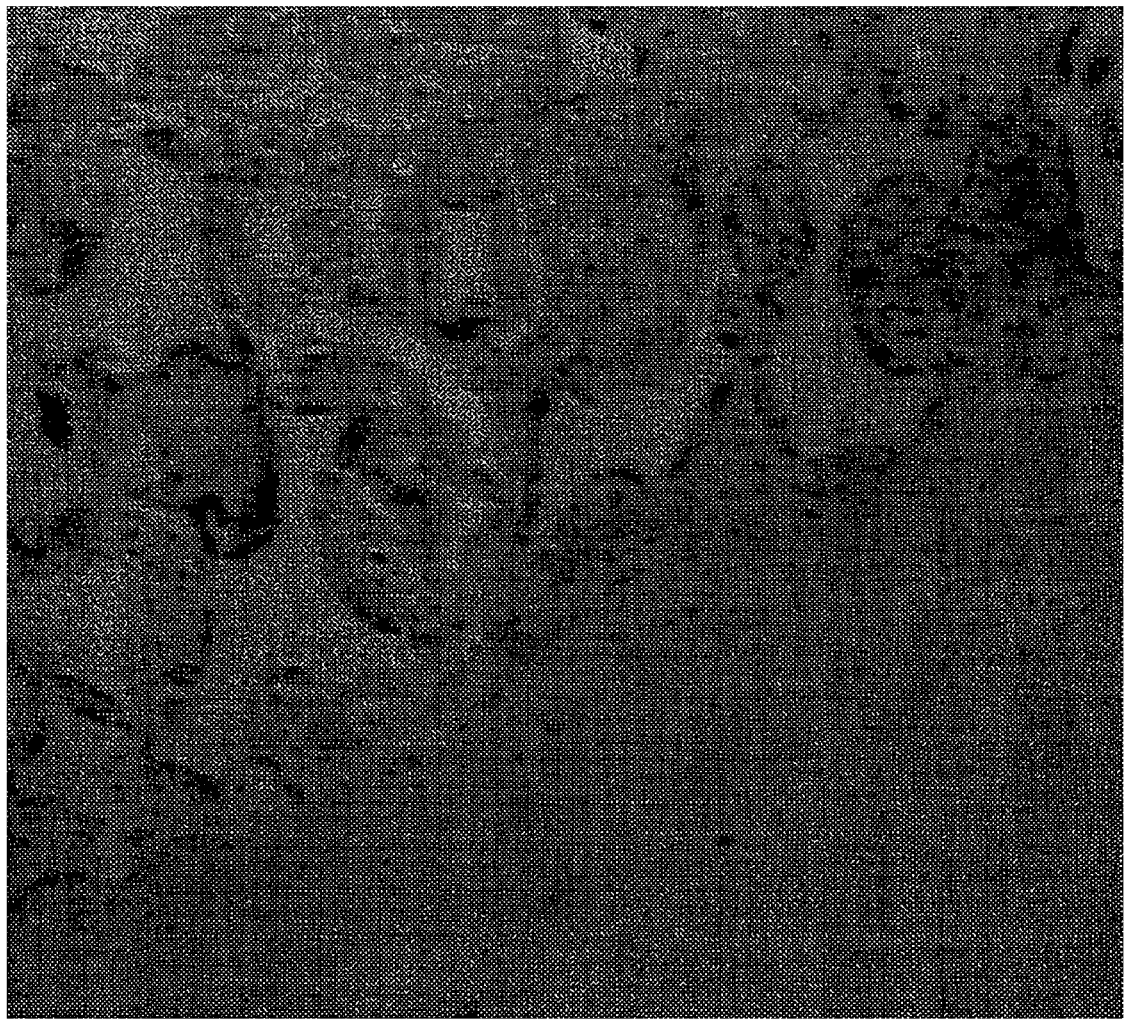
Fig. 2.6

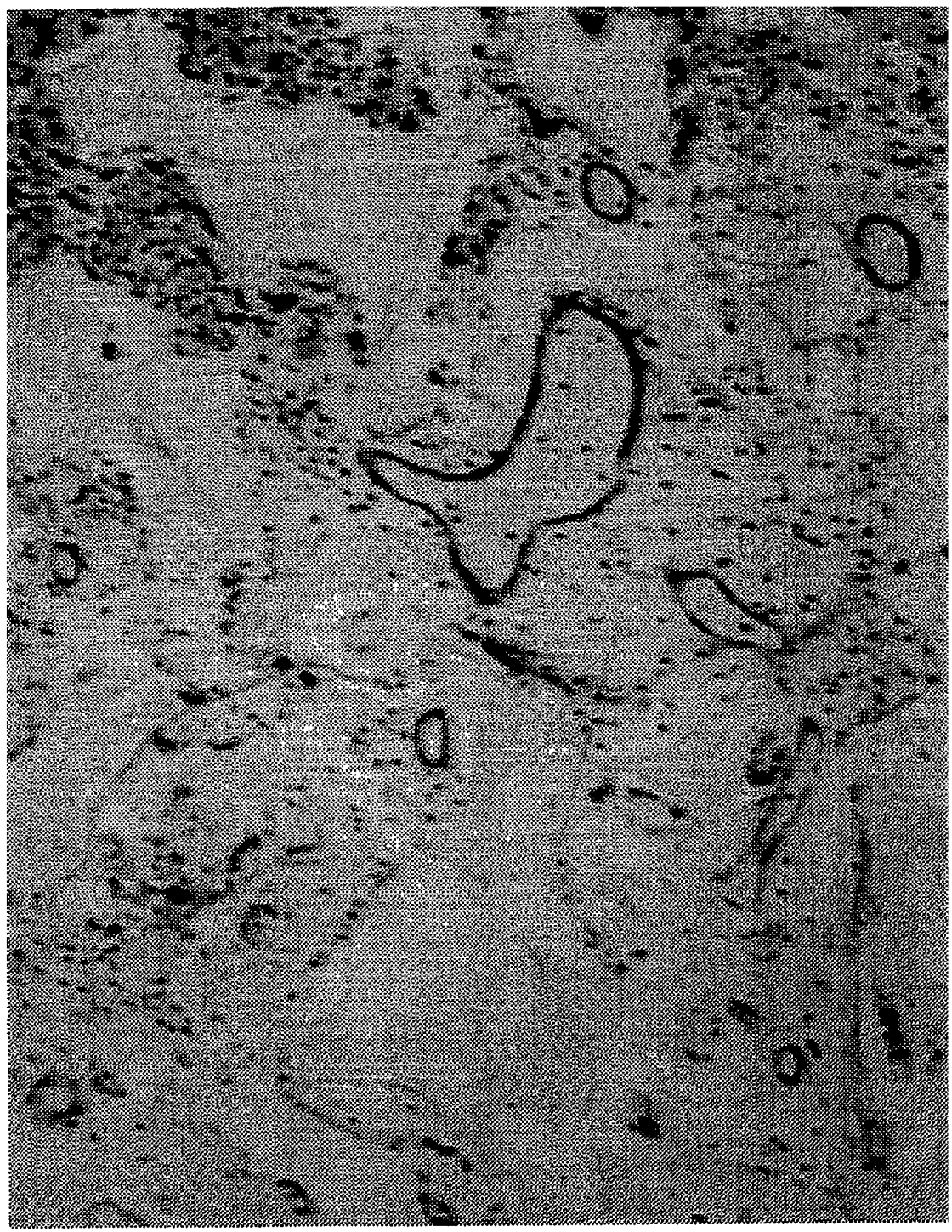
Fig. 2.7

Fig. 2.8

Fig. 2.9A

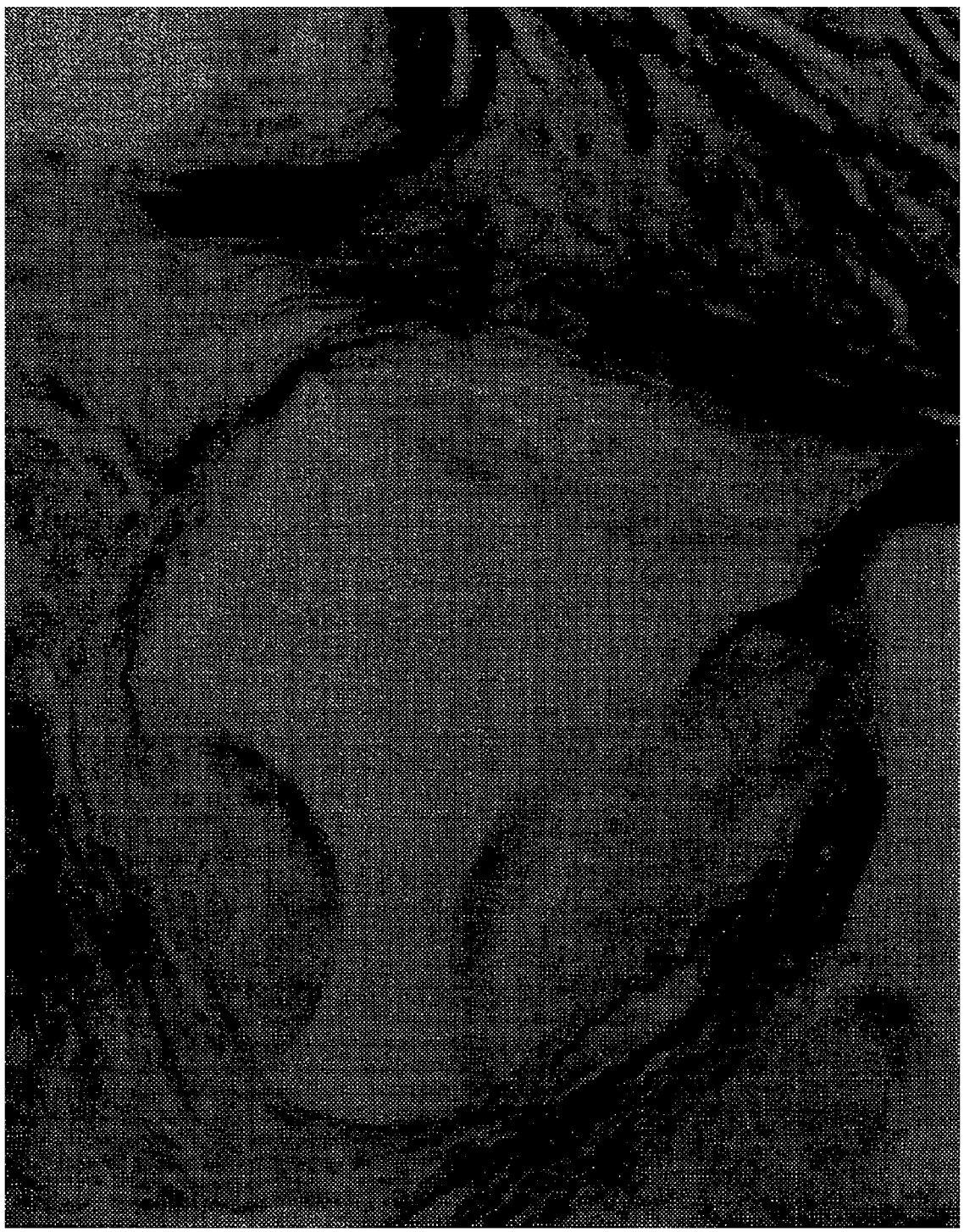
Fig. 2.9B

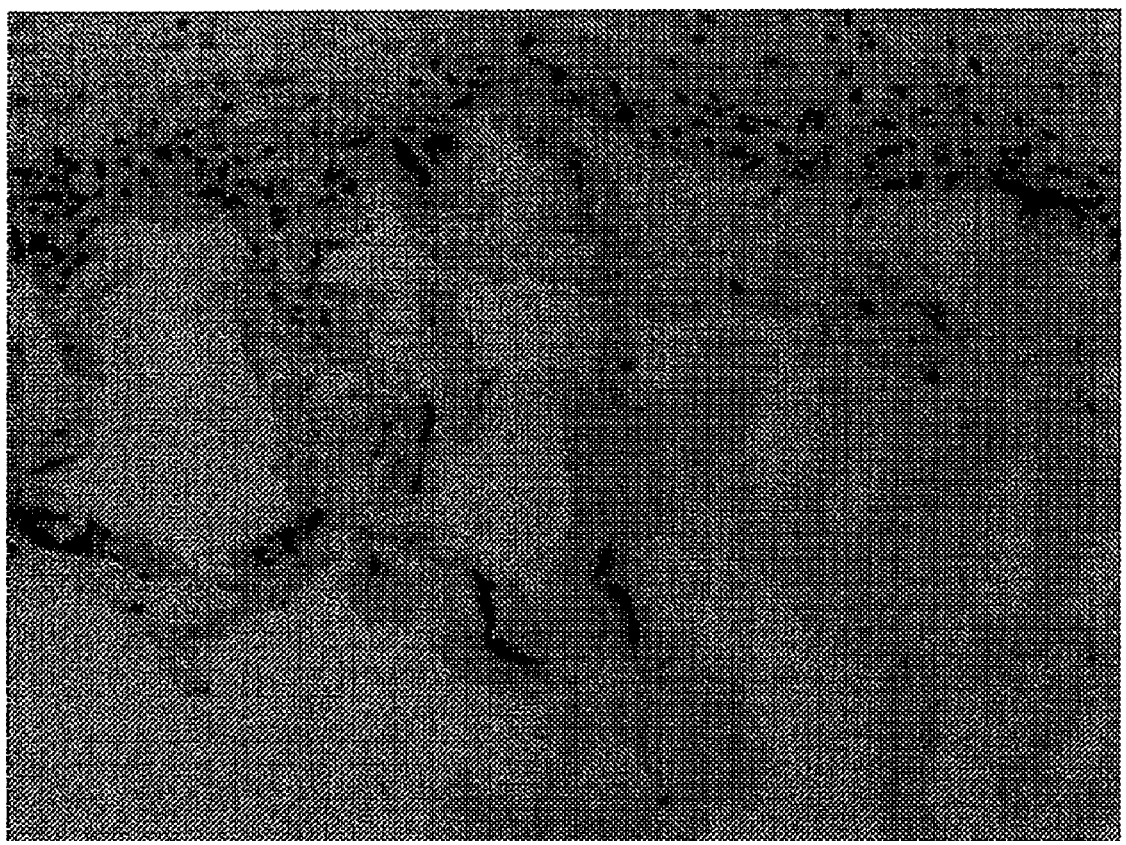
Fig. 3.1

TISSUE ENGINEERING SCAFFOLD COMPRISING POLYURETHANE MATERIAL HAVING VOIDS INTERCONNECTED BY PORES

This application is a continuation of U.S. patent application Ser. No. 11/152,780, filed Jun. 15, 2005 (now abandoned), which is a continuation of U.S. patent application Ser. No. 09/985,822 filed Nov. 6, 2001 (now abandoned), which is a continuation of PCT International Application No. PCT/IE2000/00059, filed May 8, 2000, and all of the disclosures of which are hereby incorporated by reference in their entirety.

This invention relates to a tissue engineering scaffold for cell, tissue or organ growth or reconstruction. The invention also relates to processes for preparing such a scaffold and its uses in vitro and in vivo.

BACKGROUND OF THE INVENTION

Various attempts have been made to provide 3 dimensional cellular scaffolds for tissue engineering applications. There are, however, many complex problems to be overcome. It is extremely difficult to provide a scaffold suitable for a range of applications because tissues and organs are comprised of a wide spectrum of different cell types and matrix structures. The functionality of the tissue or organ is determined by the type of cells present. Thus, for successful tissue growth a scaffold should be capable of supporting the growth of multiple cell types. Because of this serious problem it is not surprising that most of the tissue engineering materials developed to date have concentrated on a specific type of cell, a specific type of tissue or a specific organ. Even with this narrowed focus, however, attempts to produce 3 dimensional scaffolds of polymeric materials have not been entirely successful. One of the most serious problems is that cells will not readily attach directly to synthetic polymer surfaces. Even if initial cell adhesion were achievable there is the additional problem that adhered cells require nutrients and oxygen to ensure cell growth and proliferation. Waste metabolites excreted by the cells can also build up in the scaffold resulting in cell mortality.

Yet another serious problem is that conventional synthetic scaffolds for tissue engineering applications exude chemicals, which may alter, influence or precipitate a response from cells and foreign body and humoral immune systems. This alteration of the cell response is a particularly serious problem as the cell and tissue propagation converges to a conventional foreign body response. The foreign body response isolates the implant from the surrounding in vivo environment. Even if leachables could be eliminated the surface properties of the scaffold can alter, influence or precipitate a cell, foreign body or immune response.

There is a clear need for a tissue engineering scaffold which allows the cell propagation and expression process to be controlled, by the tissue environment, the scaffold geometry or growth factors present in the scaffold.

Yet another problem with conventional scaffolds is that insufficient surface is provided in 3 dimensions to construct a properly functioning tissue structure. Even where high surface area scaffolds are provided much of the surface is inaccessible to cells due to either nutrient or physical space issues.

There is therefore a need for a multi functional scaffold for use in tissue engineering applications, which will overcome at least some of these problems.

SUMMARY OF THE INVENTION

According to the invention there is provided a tissue engineering scaffold for cell, tissue or organ growth comprising a biocompatible porous polyurethane cellular material comprising a plurality of voids interconnected by pores, the cellular material having a void content from 85% to 98% and a surface area to volume ratio of from 5 to 400 $mm^2/mm^3$.

Preferably the surface area to volume ratio is from 10 to 200 $mm^2/mm^3$. Most preferably from 20 to 80 $mm^2/mm^3$.

In one embodiment of the invention the void mean diameter ranges from 20 to 300 microns, preferably from 40 to 250 microns, most preferably from 80 to 200 microns.

In one embodiment of the invention the voids are substantially spherically shaped.

In another embodiment of the invention the pore diameters are 10 to 50% of the void diameters.

Preferably the pores are generally elliptically shaped.

In one embodiment of the invention the material consists of three-dimensional cells with flattened faces at points of contact therebetween. Preferably any given cell has up to 14 faces.

In one embodiment of the invention some of the faces contain interconnecting pores between adjacent cells. Preferably the average number of interconnecting pores in any given cell is from 2 to 14, ideally from 1 to 7.

In one embodiment of the invention less than 10% of the voids have less than 2 pores.

In a further embodiment of the invention the cellular material is cleaned using a solvent with a solubility parameter of from 17 $MPa^{0.5}$ to 27 $MPa^{0.5}$.

In another embodiment of the invention the cellular material has a soft phase and hard phase.

The polar ratio of the polymer is from 1.4:1 to 10:1, preferably from 2:1 to 5:1.

In one embodiment of the invention the cellular material has a hard segment content of from 35 to 65%, preferably from 35 to 55%, ideally from 40 to 50%.

In a further embodiment of the invention the cohesive energy density of the hard phase is at least 2 $MPa^{1/2}$ greater than the cohesive energy density of the soft phase.

In another embodiment of the invention the leachables content of the cellular material is less than 1.0 mg per gram when extracted in water. Preferably the leachables content of the cellular material is less than 10 μg per gram when extracted in water, most preferably less than 0.1 μg per gram when extracted in water.

In yet a further embodiment of the invention the scaffold is manufactured from
 diphenyl methane diisocyanate (MDI) with a 2,4 MDI isomer content of less than 3%;
 a linear, long chain diol which is free of tertiary carbon linkages;
 water;
 a cross-linking agent;
 a trimerisation catalyst;
 a blowing and/or gelling catalyst; and
 a surfactant.

Preferably the diol is polytetramethylene ether glycol (PT-MEG).

Preferably the diol is a polycarbonate diol, most preferably the polycarbonate diol is a reaction product of one or more diols with a carbonate monomer.

Ideally the diol molecular weight is between 400 and 5000, most preferably between 500 and 2500.

In one embodiment of the invention the trimerisation catalyst is a carboxylate, preferably potassium acetate.

Most preferably the potassium acetate is present in the reaction formulation in an amount of from 0.02% to 0.12% by mass of the formulation.

In a further embodiment the cross-linking agent is present in the reaction formulation in an amount of from 1% to 5% by mass. Preferably the cross-linking agent is trialkanol amine. The cross-linking agent may be triethanolamine.

In one embodiment of the invention the isocyanate index of the reaction formulation is from 1.03 to 1.20, preferably approximately 1.13.

In a further embodiment of the invention the reaction formulation includes a chain extender. Preferably the chain extender is a linear aliphatic diol. Most preferably 1,4 butane diol.

In one instance the chain extender is present in the formulation in an amount of less than 7% by mass, preferably in an amount of less than 4% by mass.

In one embodiment of the invention water is present in the reaction formulation in an amount of from 0.6% to 1.8% by mass.

The invention also provides a formulation for forming a tissue engineering scaffold comprising:—
 an isocyanate;
 a chain extender;
 water; and
 a cross linking agent, wherein the isocyanate is MDI with a 4,4 MDI isomer content of greater than 97% and wherein the isocyanate index of the reaction formulation is from 1.03 to 1.20.

Preferably the isocyanate index is approximately 1.13.

The invention also provides a formulation for forming a tissue engineering scaffold comprising:
 diphenyl methane diisocyanate (MDI) with a 2,4 MDI isomer content of less than 3%;
 a linear, long chain diol which is free of tertiary carbon linkages;
 water;
 a cross-linking agent;
 a trimerisation catalyst;
 a blowing and/or gelling catalyst; and
 a surfactant.

In one case the diol is polytetramethylene ether glycol (PTMEG).

Alternatively the diol is a polycarbonate diol. Ideally the polycarbonate diol is a reaction product of one or more diols with a carbonate monomer.

Preferably the diol molecular weight is between 400 and 5000, most preferably between 500 and 2500.

In one embodiment the trimerisation catalyst is a carboxylate, preferably a potassium acetate. In this case potassium acetate is present in the reaction formulation in an amount of from 0.02% to 0.12% by mass of the formulation.

In another embodiment of the invention the cross-linking agent is present in the reaction formulation in an amount of from 1% to 5% by mass. Preferably the cross-linking agent is trialkanol amine. Most preferably the cross-linking agent is triethanolamine.

In one embodiment of the invention the isocyanate index of the reaction formulation is from 1.03 to 1.20, ideally approximately 1.13.

In another embodiment the reaction formulation includes a chain extender. Preferably the chain extender is a linear aliphatic diol, most preferably 1,4 butane diol.

In a further embodiment the chain extender is present in the formulation in an amount of less than 7% by mass, preferably in an amount of less than 4% by mass.

In one embodiment of the invention water is present in the reaction formulation in an amount of from 0.6% to 1.8% by mass.

The invention further provides a process for preparing a tissue engineering scaffold comprising the steps of:—
 preparing a isocyanate terminated prepolymer in an excess of isocyanate;
 preparing a polyol reaction mixture comprising a polyol, a chain extender, a catalyst, a blowing agent, a cross linking agent, a catalyst and a surfactant;
 mixing the prepolymer and the polyol
 dispensing the mixed reaction ingredients into a mould;
 post curing the reaction ingredients; and
 solvent extracting the material with a solvent having a solubility parameter of from 17 to 27 $MPa^{0.5}$.

The process preferably includes the step, prior to solvent extraction, of crushing the moulded cellular material thus formed to increase the open cell content of the material.

In one embodiment the prepolymer is prepared from a prepolymer reaction mixture at a temperature of from 70 to 80° C. Preferably the prepolymer reaction mixture is reacted for a period of from 1 to 2 hours.

The prepolymer reaction mixture is preferably stirred continuously under a dry inert atmosphere.

Preferably the rotational mixing element for mixing the prepolymer reaction mixture is configured to generate turbulent mixing.

In one embodiment of the invention during moulding the mould temperature is maintained at not less than 30° C., preferably from 50 to 80° C.

The process preferably also includes the step of venting the mould during moulding to facilitate free rise. Preferably the volume of the mould is such as to facilitate at least a ten fold volumetric expansion of the reaction ingredients. Most preferably the volume of the mould is such as to facilitate a less than 50 fold volumetric expansion of the reaction ingredients.

In one embodiment of the invention post curing is carried out at a temperature of at least 20° C. for a period of at least 30 minutes. Preferably the post-curing is carried out at a temperature of approximately 80° C.

Ideally the post-curing is carried out in a post-cure oven.

Preferably the post-curing is carried out in a $CO_2$ rich environment.

In one embodiment of the invention the moulded cellular material is crushed by greater than 80% of the pre-crushed volume of the material. Preferably the crushing is carried out in the presence of a solvent.

In one embodiment of the invention the extraction solvent used for solvent extraction has a polar component of its solubility parameter in excess of 3 $MPa^{0.5}$.

In a further embodiment of the invention the solubility parameter of the extraction solvent is within ±4 $Mpa^{0.5}$ of the solubility parameter of the polymeric material or its phases.

In yet another embodiment of the invention the vapour pressure of the extraction solvent is greater than 2 kPa at 25° C. Preferably the vapour pressure of the extraction solvent is greater than 5 kPa at 25° C. Most preferably greater than 10 kPa at 25° C.

Ideally the extraction solvent has a solubility parameter of from 18 to 24 $MPa^{0.5}$.

In one embodiment of the invention the extraction solvent used for solvent extraction is water miscible.

In another embodiment of the invention the extraction solvent used for solvent extraction is a swelling solvent. Preferably the swelling solvent swells the material by more than 30%, most preferably by more than 100%. Ideally by more than 150%.

In one embodiment of the invention the extraction solvent used for solvent extraction includes tetrahydrofuran (THF).

In another embodiment of the invention the extraction solvent used for solvent extraction includes methyl ethyl ketone (MEK).

Preferably the solvent extraction step is carried out for a period of at least 2 hours at room temperature.

Most preferably the process includes the step of de-swelling the solvent swollen polymeric material.

Preferably the polymeric material is de-swelled by contacting the solvent swollen polymeric material with a non-solvent which is miscible with the extraction solvent.

In one embodiment of the invention the process includes the step of drying the polymeric material to substantially remove solvent residues.

Preferably the process also includes the step, prior to drying, of extracting the polymeric material with water.

In one embodiment of the invention the polymeric material is extracted with a number of extraction solvents.

Preferably the solvent extractions are carried out sequentially.

Most preferably the non solvent is an alcohol.

In one embodiment of the invention the non solvent is added to the solvent swollen polymeric material in an amount and at a rate to maintain a low concentration gradient.

In another embodiment of the invention the de-swelling is carried out at a temperature of less than 40° C.

STATEMENTS OF THE INVENTION

The major advantages of the invention fall into two critical, but related and complimentary, areas in the development of a scaffold, the first is the hosts response to the scaffold and the second is the ability of the scaffold to match the compliance of the tissue being engineered.

The invention promotes a highly desirable host response.

The development of multifunctional tissue engineering scaffolds has been hampered by the fact that in order to generate a properly functioning tissue it has been necessary to resorb the scaffold. The resorption of the scaffold opens up space for fluid and cellular communication.

However, currently available materials cannot be resorbed without generating chemical by-products. These chemicals are identified by the immune system and alter the host response to the scaffold. Even biopolymers are processed using synthetic chemicals, which are liberated during the resorption process.

The void content of the materials of the invention is exceptionally large. This means that very little synthetic material is used in the construction of the scaffold and makes issues of bioresorption less significant.

The scaffold of this invention is treated by a solvent extraction technique, which ensures that no chemicals leach from the scaffold, in use. Thus, the scaffold is substantially chemically neutral to its environment and does not alter, influence or precipitate a response from cells and/or the foreign body and humoral immune system. Furthermore the removal of the leachables ensures that a homogenous surface chemistry is presented throughout the entire surface of the scaffold.

The absence of leachables, the phase separated morphology and the hydrophilic/hydrophobic surface chemistry of the scaffold of this invention produce an atypical foreign body response which inhibits the formation of thick fibrous encapsulation. Fibrous encapsulation is the term assigned to the process by which a foreign object is walled off from the surrounding tissue. Fibrous encapsulation is induced by a host defense mechanism, wherein granulation tissue isolating the implant from the surrounding in vivo environment is formed.

The scaffolds of this invention are non-cytotoxic. A cytotoxicity test, which determines the effect of biomaterial extract media on the lysis of cells or the inhibition of cell growth resulted in a grade zero response. This is the lowest cytotoxic response possible from the test method. This verifies the effectiveness of materials and processes of the invention in eliminating leachables.

The inert nature of the scaffold was further demonstrated by implanting scaffolds of this invention in laboratory animals. A geometry precipitated chronic inflammatory response was observed. The material was stable at 6 months. The absence of any lymphocyte response was confirmed.

A particularly unique feature of the scaffold is the presence of a large population of fat cells in close proximity to the ends of the scaffold. Fat cells are essentially large globules of fat (coalesced triacyl glycerides) surrounded by a cytoplasm with a bulging nucleus. The positioning of the fat cells in close proximity to the scaffold demonstrates the excellent compatibility between the implant and the neighbouring muscle.

The scaffold is designed to match the compliance of the tissue being engineered.

The response to the scaffold is geometry and morphology driven. The implications of these features is very significant. It means that the tissue structures which propagate through the scaffold in vivo depend on where the scaffold is placed, the geometry, morphology or hydrophilicity properties of the scaffold and the chemical environment. The chemical environment can be altered with growth factors, chemoattractants or other agents which alter the path of tissue structure development.

The physical properties of the scaffold can be modified so as to match the compliance of the tissue structure being engineered. In the tissue engineering scaffold of the invention there is provided a huge surface area in three dimensions available for cell adherence. The scaffold surfaces are designed to promote cell adhesion. The interconnecting pores within the scaffold have a multi-dimensional aspect, which facilitates the availability of nutrients and oxygen to the adhered cells, and ensure that the waste metabolites are not retained in the scaffold thus optimizing cell growth.

Communication between cells is important in the regulation of normal physiological function in organs and tissues. Cellular communication is facilitated by chemical messengers acting in conjunction with plasma membrane bound signaling molecules or through gap junctions. The open pore 3 dimensional aspect of the tissue engineering scaffolds of the current invention ensures that cellular communication is maintained. This feature is highly desirable for organ generation or reconstruction.

The scaffolds of the invention also facilitate the infiltration and co-existence of multiple cell types within the biomaterial. This is particularly important in applications in tissue/organ growth or reconstruction, where multiple cell types must co-exist.

The scaffolds of this invention have been shown to support several cell types including cells secreting structural proteins and cells that produce proteins characterizing organ function. The ability of the scaffold to facilitate the co-existence of multiple cell types together and its ability to support protein secreting cells demonstrates the applicability of the scaffold in organ growth in vitro or in vivo and in organ reconstruction.

A further advantage of the scaffold of this invention is that the phenotypic expression of cells is not altered as a result of exposure to the biomaterial. Phenotypic expression is the term used to define the ability of the cell to express the cellular genotype. Individual cells have different "activated" genes on their cell genome and the expression of these active genes is important in demonstrating cellular function. Frequently cellular activity is expressed as synthesis of proteins or glycoproteins, encoded on the DNA sequence. Collagen has been observed within the biomaterial of the invention after implantation, which demonstrates the ability of myofibroblasts cells within the biomaterial implant to express their genotype as collagen (phenotype).

A particularly important property of the scaffold is its ability to support a 3 dimensional capillary network. This phenomenon is termed angiogenesis or neovascularisation. The formation of the 3 dimensional capillary bed throughout the biomaterial scaffold is advantageous in ensuring the long-term viability of larger engineered structures in vivo.

BRIEF DESCRIPTION OF THE DRAWINGS

FIG. 1.0 is a scanning electron micrograph (SEM) of an article of the invention showing the voids of a scaffold and the interconnecting pores between the voids;

FIG. 1.1 is a SEM image of Polyether polyurethane biomaterial placed in a chamber with a 0.45 µm filter, implanted subcutaneously in the rat animal model and explanted after 8 weeks. Note the integrity of the voids of the biomaterial. The structure of the voids is similar to that for the control sample (FIG. 1.2) demonstrating no evidence of Environmental Stress Cracking (ESC);

FIG. 1.2 is a SEM image of Polyether polyurethane biomaterial control sample which was not implanted in the rat model;

FIG. 1.3 is a SEM image of Polyether polyurethane biomaterial placed in a chamber with a 0.45 µm filter, implanted subcutaneously in the rat animal model and explanted after 8 weeks. As in FIG. 1.1, note the integrity of the voids of the biomaterial. The structure of the voids is similar to that for the control sample (FIG. 1.2) demonstrating no evidence of ESC;

FIG. 1.4 is a SEM image (at high magnification) of Polyether polyurethane) biomaterial placed in a chamber with a 0.45 µm filter, implanted subcutaneously in the rat animal model and explanted after 8 weeks. Note the integrity of the void of the biomaterial. The structure of the voids is similar to that for the control sample (FIG. 1.2) demonstrating no evidence of ESC;

FIG. 1.5 is a SEM image of Polyether polyurethane biomaterial placed in a chamber with a 3.0 µm filter, implanted subcutaneously in the rat animal model and explanted after 26 weeks. Note the integrity of the voids of the biomaterial and the cellular deposition on the biomaterial. There is no evidence in this SEM image of ESC;

FIG. 2.1 is a photomicrograph of the scaffold of Example 1 stained with Haemoxylin and Eosin (H&E), 12 weeks following implantation. Note the presence of numerous macrophage cells throughout the scaffold and the presence of blood capillaries (indicated by the arrow A) in the centre of the scaffold;

FIG. 2.2 represents images from 2 rat explants at 26 weeks, which were stained positive with rat monoclonal antibodies to $ED_1$ cells (immature macrophage and monocytes);

FIG. 2.3 is a photomicrograph (3.2×) of the scaffold of Example 1, explanted at 12 weeks and stained with H&E. Note the absence of a fibrotic layer between the scaffold and the muscle;

FIG. 2.4 is a photomicrograph (3.2×) of an intramuscular implant of Example 1, explanted at 26 weeks and stained with H&E. Note the presence of translucent fat cells to the left of the implant, as highlighted by the arrows B and C;

FIG. 2.5 represents images from a rat explant at 26 weeks, which stained negative with $CD^4$ and $CD^8$ rat monoclonal antibodies. There was no evidence of $CD^4$ or $CD^8$ lymphocytes throughout the scaffold;

FIG. 2.6 is a photomicrograph (10×) of the scaffold at 8 weeks after venous implantation. Numerous inflammatory cells (macrophage) are evident throughout the scaffold. Also note there is no fibrotic wall between the scaffold and the venous wall;

FIG. 2.7 illustrates the expression of α-smooth muscle actin throughout the scaffold 8 weeks post implantation. The α-smooth muscle actin is present in the walls of the capillaries forming the capillary bed;

FIG. 2.8 is a photomicrograph (50×) of the scaffold 8 weeks after venous implantation. Note the blood capillary in the top left of the photomicrograph with red blood cells present in the lumen of the capillary. The flattened elongated cells defining the capillary wall are characteristic of the morphology of endothelial cells;

FIG. 2.9*a* is a photomicrograph of collagen deposition stained blue by MSB one week following implantation of the scaffold of Example 1;

FIG. 2.9*b* is a 40× magnification of a photomicrograph of collagen deposition stained blue by MSB 4 weeks following implantation of the scaffold of Example 1; and FIG. 3.1 is a photomicrograph of a polycarbonate polyurethane material of the invention

DETAILED DESCRIPTION

The invention will be more clearly understood from the following description thereof.
Geometry The scaffolds of this invention have unique geometric characteristics that make them very suitable for tissue engineering applications.

A Scanning Electron Microscopy (SEM) image of an article of this invention is provided in FIG. 1.0. This image illustrates the voids of the scaffold and the interconnecting pores between the voids.

The scaffold is characterized geometrically in that it consists of a myriad of regularly shaped close packed and interpenetrating voids.

These voids are characterized in that they are approximately spherical in shape.

The material void space is further defined in that it contains pores that interconnect the spherical voids. The void geometry is further defined in that the spherical voids impinge on one another to create faces or pores. The spherical voids have a smooth surface and are between 10 and 300 microns in mean diameter. The interconnecting pores are between 20 and 50% of the spherical void diameter. There are between 1 and 14 interconnecting pores in a cell. The average number of pores per cell varies between 1 and 7.

The surface area to volume ratio is between 5 $mm^2/mm^3$ and 350 $mm^2/mm^3$. More preferably the surface area to volume ratio is greater than 20 $mm^2/mm^3$. Even more preferably the surface area to volume ratio is greater than 50 $mm^2/mm^3$.

While this invention provides for a massive surface area to volume ratio α crucial aspect of the surface area provided is that virtually the entire surface area created by the invention is accessible to cells and facilitates cell adhesion. This is in stark contrast to the type of surfaces created by phase inversion or freeze drying techniques where irregularly shaped structures preclude cell access or adhesion.

The calculated relationships between void diameter, pore diameter, number of pores per void and the surface to volume ratio are shown on the following table;

The void diameter, pore diameter (set at 20% and 50% of the diameter of the void, for the purposes of this example) and the number of pores per void are variable factors derived from a model of void positioning. The number of voids per cubic millimetre and the surface to volume area ratio for a sample of void diameters, pore diameters and number of pores in a given void are calculated and presented in the table.

| Void φ (μm) | Pore φ (μm) | No. of voids/mm³ | Avg. no. of pores per void | SA/V(mm²/mm³) (curved surface) |
|---|---|---|---|---|
| 300 | 150 | 81 | 12 | 4.6 |
| 300 | 60 | 56 | 12 | 14.0 |
| 300 | 150 | 81 | 6 | 13.7 |
| 300 | 60 | 56 | 6 | 14.9 |
| 300 | 150 | 81 | 2 | 19.8 |
| 300 | 60 | 56 | 2 | 15.5 |
| 200 | 100 | 273 | 12 | 6.9 |
| 200 | 40 | 189 | 12 | 20.9 |
| 200 | 100 | 273 | 6 | 20.6 |
| 200 | 40 | 189 | 6 | 22.3 |
| 200 | 100 | 273 | 2 | 29.7 |
| 200 | 40 | 189 | 2 | 23.2 |
| 100 | 50 | 2184 | 12 | 13.9 |
| 100 | 20 | 1508 | 12 | 41.9 |
| 100 | 50 | 2184 | 6 | 41.2 |
| 100 | 20 | 1508 | 6 | 44.6 |
| 100 | 50 | 2184 | 2 | 59.5 |
| 100 | 20 | 1508 | 2 | 46.4 |
| 20 | 10 | 272989 | 12 | 69.3 |
| 20 | 4 | 188508 | 12 | 209.5 |
| 20 | 10 | 272989 | 6 | 323.1 |
| 20 | 4 | 188508 | 6 | 223.1 |
| 20 | 10 | 272989 | 2 | 336.3 |
| 20 | 4 | 188508 | 2 | 232.2 |

The above table assumes that all voids are the same size. In reality there is a distribution of void sizes within any scaffold. The void diameters in the table can be interpreted as average values.

In general increasing the surface area to volume ratios is desirable for tissue engineering scaffolds and are possible with this invention. In general voids larger than 300 microns are not desired per this invention. However, a small number of voids in excess of 300 microns improves the ease with which fluids can migrate to and from the core of the scaffold. This becomes more important when engineering large organs as these larger spaces facilitate good fluid communication throughout the scaffold/organ. Indeed in large organs or tissue applications channels may be machined through the scaffold to optimize fluid transfer.

Pore diameters less than 30 microns are less desirable because they restrict fluid movement and this makes larger tissue engineering structures difficult to nourish and detoxify. Fluid movement is improved per this invention by increasing the number of pores per void, increasing the pore diameter and/or increasing the void diameter.

Surface Characteristics

Adherent cell lines are the most important in tissue engineering applications as they make up the bulk of cells in tissue and organs. The adhesion of cells to the surface of a scaffold is a critical function of a tissue engineering substrate. Conventional substrates employ enzyme coated polystyrene surfaces to achieve adhesion. This invention provides a substratum that achieves cell adhesion without the need for enzymatic or synthetic coatings. The materials of this invention are two phase materials and contains both hydrophilic conferring atoms and hydrophobic conferring atoms. The ratio of hydrophobic atoms to hydrophilic atoms in the phases is controlled so as to achieve good cell attachment.

Achieving the optimum surface properties of the materials of this invention involves simultaneously controlling the properties of phase separation and hydrophobicity. Phase separation is a morphological characteristic while hydrophobicity is a molecular characteristic. In a preferred embodiment the materials of this invention provide a scaffold with a phase separated morphology and a controlled percentage of hydrophilic and hydrophobic conferring atoms.

Phase separation is driven by intermolecular interactions. Molecular interactions of polymers are characterized generally as dispersion interactions, polar interactions and hydrogen bonding interactions. Solubility parameter values provide a gross assessment as to the strength of the molecular interactions of a linkage chain, molecule or polymer. Phase separation occurs when the intermolecular interactions of two components are different. In a preferred embodiment of the current invention the difference in the solubility parameter value of the soft phase and the hard phase is greater than 2 $MPa^{1/2}$. The solubility parameter of the hard phase is usually higher than the soft phase. This is driven by the content of cyclic groups (dispersion interactions) and hydrogen bonding groups (H bonding interactions) in the hard phase.

The polyurethane scaffolds of this invention have the advantage that they are two-phase materials and it is possible to adjust the hydrophilic character of the phases independently. It is further possible to adjust the interchain attraction forces of the phases independently.

The polar characteristics of the phases are described in terms of the ratio of hydrophilic conferring atoms to hydrophobic conferring atoms. For the materials of this invention this ratio is reduced to a ratio of carbon atoms to the sum of the nitrogen and oxygen atoms in the phase, or in the system. The ratio is termed the polar ratio.

Polar Ratio=(No. Carbon Atoms):(No. Nitrogen+Oxygen Atoms)

The materials of this invention are primarily composed of hydrogen, carbon oxygen and nitrogen. Hydrogen is ignored in the calculation of the polar ratio. Adjusting the ratio of hydrophilic groups to the ratio of hydrophobic groups in either the soft or hard phase of the material can alter the hydrophilic/phobic characteristics of the substrate. Nitrogen and oxygen are highly electronegative and form polar bonds with atoms of lower electro-negativity (EN) value. These polar bonds confer a hydrophilic character to the material. Atoms with similar EN values form non-polar covalent bonds and tend to confer a hydrophobic character. Clearly increasing or decreasing the nitrogen or oxygen content in either phase will alter the hydrophilicity of the material.

In a preferred embodiment the polar ratio for the polymer scaffolds of the invention is between 1.5:1 and 10:1. More preferably the polar ratio is between 2.0:1 and 5:1.

The polar ratio for the hard segment of an MDI and water based hard phase is 4.67:1. The polar ratio for a TDI and water based system is 2.7:1. The polar ratio for the scaffold of Example 1 is 3.96:1.

Higher polar ratio values for either phase or for the polymer in its entirety will result in a substratum with a reduced wettability to water. As physiological conditions are water based increasing polar ratio of the substrate reduces the permeability of nutrients through the matrix. However decreasing the polar ratio renders the scaffold surface non-adherent to cells. The preferred range for the polar ratio for the polymer system is 2.5:1 to 4:1. Optimum polar ratio values can be achieved by making one phase hydrophilic and the other phase hydrophobic while still achieving an overall polar ratio value within the above range.

Hard Segment Content

The materials of this invention are two phase materials. The hard phase is generated by the reaction of an isocyanate with small chain molecules. Typically, the small chain molecules are diols, amines, alkanol amines or water. Preferably the chain extenders are diols or water. The second phase of the material is referred to as the soft phase and is composed primarily of polyol. The two phases are preferably different and are largely immiscible. This allows the two phases separate into distinct domains. This phase separated domain structure confers optimal characteristics to the material.

The phase separation of conventional polyurethanes is assisted by hard phase order and crystallization in the hard phase. Cross linking is generally considered to be disadvantageous to the hard phase order. The cross linking of the scaffolds of the current invention is largely confined to the hard phase.

Phase separation is enhanced by achieving most of the crosslinking in the hard phase. The use of a difunctional polyol is preferred.

The Hard Segment Content is defined as follows:

$$\{M_{\cdot(isocyanate)} + M_{\cdot(chain\ extender)} + M_{\cdot(crosslinker)} + M_{\cdot(water)} - M_{\cdot(CO_2)}\} / \{M_{\cdot(isocyanate)} + M_{\cdot(chain\ extender)} + M_{\cdot(crosslinker)} + M_{\cdot(water)} + M_{\cdot(polyol)} - M \cdot (CO_2)\}$$

Where M is the mass of a material used in or generated by the reaction.

Materials

The chemical precursors to the material scaffolds of this invention are selected on the following basis:

Maximizing Surface Area

In order to manufacture materials with the massive surface to volume ratios per the materials of this invention a blowing step is necessary in the manufacturing process. Blowing is the preferred method of void creation. Blowing has the advantage in that voids pack relative to their neighbors and produce a more homogenous structure. This blowing step should be carried out as the material molecular weight increases or prior to its increase. In other words the blowing occurs while the material is in a low viscosity state. Preferably the starting viscosities of the components is less than 4000 cps. More preferably the viscosity of the pre-polymer and polyol of this invention is less than 200 cps.

3-Dimensional Molecular Structure:

The scaffolds of this invention are 3-dimensional molecular structures.

The cross-linked molecular structure is critical to the manufacture of leachable free structures of the invention. The chemical precursors must contain at least one trifunctional ingredient.

Hydrophilicity/Hydrophobicity

The materials of this invention are neither highly hydrophilic nor are they highly hydrophobic. The chemical precursors thus contain both hydrophobic conferring atoms and hydrophilic conferring atoms.

Polyurethanes are the preferred materials of this invention. The chemical precursors are thus an isocyanate, a polyol, a crosslinking entity, a blowing agent and a chain extender. Catalysts and surfactants are necessary to control the reaction.

Leachable Free Scaffold

The 3-dimensional molecular structure is critical to achieving the physical and chemical characteristics of the invention. The three dimensional aspect is achieved either by incorporating a trifunctional entity within the formulation or by employing an isocyanate index in excess of 1. The preferred materials of this invention use both a crosslinking agent and a high isocyanate index. The advantage of using both approaches is that the crosslinking agent stabilizes the material during the blowing process and the excess isocyanate reacts with available active hydrogen sites and minimizes the levels of leachables.

An objective of the present invention is to provide tissue-engineering scaffolds that are virtually free of leachables. Leachable free scaffolds are produced per this invention by solvent extraction. Solvent extraction techniques are well known. Conventional solvent extraction involves exposing a polymer to a solvent that has minimal effects on the polymer. Low molecular weight chemicals migrate from the near surface region into the solvent.

The solvent extraction technique of the current invention is unique in that the solvent is selected such that it has a massive volume swelling impact on the substrate. With linear polymers of conventional PLA and PGLA tissue scaffolds this swelling would catastrophically destroy the physical structure. The crosslink density of the materials of this invention allows the materials to deform massively without complete loss of physical structure. Indeed the crosslinks provide a memory of the unswollen physical structure. At large volume swelling ratios, significant amounts of additives, unreacted monomers, oligomers and even high molecular weight linear polymer are liberated into the solvent phase. The mass loss in this type of extraction can be in excess of 10%. While this huge loss of leachables from the structure provides for a leachable free scaffold, recovery of the physical structure is a difficult problem post extraction. Additionally the swollen polymer is very tacky. The surfaces of voids can stick together, pores can become closed and a general loss of physical structure results from any gross mechanical deformations. The processes of the invention overcome these difficulties.

While the cross-links provide a memory of the original molecular structure, the recovery process brings the scaffold back to its original geometry.

It is an objective of this invention to provide the lowest level of leachables possible. Leachable levels can be measured gravimetrically or analytically (chromatography). In a preferred embodiment, HPLC grade water extraction of the scaffold at 40° C. should produce a leachables content less than 1.0 mg per g. More preferably the water extracted leachables content is less than 10 µg per g. Even more preferably the water extracted leachables content is less than 0.1 µg per g. Even more preferably the water extracted leachables content is less than 10.0 ng per g. Extraction times in excess of 12 hours should be employed. These levels are near or below the level of detection for many analytical systems and may be demonstrated by extrapolation.

In another embodiment the exposure of the processed scaffold to a solvent whose solubility parameter is between 18 $MPa^{1/2}$ and 24 $MPa^{1/2}$, at 40° C., should produce a leachables content less than 10.0 mg per g in the solvent. More preferably the solvent extracted leachables content is less than 100 µg per g. Even more preferably the solvent extracted leachables content of the scaffold is less than 10.0 µg per g. Suitable solvents for this assessment include MEK, DMA and THF.

A preferred embodiment involves the use of solvents, which provide the maximum swelling. The volume swelling during solvent extraction should be above 30%. More preferably the solvent swelling should be in excess of 100%. Even more preferable is solvent swelling in excess of 150%. The level of solvent swelling decreases as the average molecular weight between cross-links decreases. However a minimum cross-link density is necessary to provide solvent swelling memory.

The molecular weight between cross-links of the material should preferably be between 300 and 6000. Preferably the molecular weight between the cross-links of the material is between 800 and 2000.

The removal of additives, unreacted monomers, oligomers and even high molecular weight linear polymer from the material produces a material whose molecular weight is massive. Indeed the entire tissue scaffold is one massive molecule. This is not true of cross linked materials in general as the statistical nature of polymer synthesis ensures that there is always an abundance of low molecular weight material and high molecular weight linear polymer in the midst of the cross linked structure. The molecular weight of the materials of this invention can be described as apparently infinite. These molecular characteristics make these materials unique and provide significant advantages over existing scaffold materials.

EXAMPLES

The unique features of the tissue engineering scaffolds of this invention will be demonstrated by the following examples.

Example A

For the preparation of polyether urethane tissue engineering scaffold a polyol resin and an isocyanate pre-polymer are prepared. In the preparation of the polyol resin the following raw materials are added to a heated round bottom flask and mixed;

| Raw material | Function | Quantity (php) |
| --- | --- | --- |
| PTMEG (MW 1000)[1] | Polyol | 100 |
| Triethanolamine[2] | Cross-linking agent | 4.6 |
| Water[3] | Blowing agent | 2.56 |
| 1,4 Butanediol[4] | Chain extender | 8.05 |
| BF 2270[5] | Surfactant | 1.0 |
| RC Catalyst 105[6] | Gelling catalyst | 2.96 |
| Desmorapid PP[7] | Blowing catalyst | 0.34 |
| Kac/Deg[8] | Trimerisation catalyst | 0.73 |

[1]Terathane (Du Pont)
[2]Sigma Aldrich
[3]Sigma Aldrich
[4]Sigma Aldrich
[5]Th GoldSchmidt
[6]DABCO and Diethylene Glycol (Rhein Chemie) at a ratio of 33.3:66.7
[7]Whitchem
[8]Potassium acetate and Diethylene Glycol (Sigma Aldrich) at a ratio of 30:70

The materials are mixed at 50 to 60° C. for a minimum of 25-30 minutes.

An isocyanate pre-polymer with an NCO content of 15.6% was prepared by charging flake MDI (Desmodur 44M flakes from Bayer with a 2,4'-isomer content of 1.7%) into a heated round bottom flask and allowing the flakes to melt. The MDI is mixed thoroughly with PTMEG (Terathane MW 1000) at 70 to 80° C. for 60 to 90 minutes. The reaction vessel is purged with dry nitrogen to eliminate moisture from the reaction vessel.

The scaffold is prepared using metering, mixing and dispensing equipment manufactured by 2 KM (Germany). The polyol resin and Isocyanate pre-polymer are added to separate reservoirs and a vacuum is applied to remove air from the materials. This removal of air from the materials controls the number of very large voids throughout the material. The materials are mixed at a speed of 5000 rpm. The materials at a temperature of 40° C., are dispensed into a preheated silicone mould at a temperature of 80° C. to 90° C. at an isocyanate index of 1.13. The mould is placed in a $CO_2$ vented oven, at a temperature of 90° C. for a minimum of 90 minutes. The biomaterial is reticulated by a hand press and solvent extraction is carried out in Methyl Ethyl Ketone (MEK).

The scaffold material was immersed in MEK in a flask. The flask was stoppered and placed in a water filled ultrasonic bath. The bath was at room temperature and the flask was sonified for 6 hours. After the 6 hours the contents of the flask were transferred to a larger vessel. Non-solvent, water, was added to the vessel over a 3 hour period, so the final concentration of solvent was below 5%.

Samples were taken post curing to perform the tests listed below.

Results

| Test | Result |
| --- | --- |
| Void Content | 90% |
| Polar ratio | 3.96 |
| Average void diameter | 100-120 μm |
| Average Pore diameter | 10-30 μm |
| Surface:Volume ratio | 40 to 50 $mm^2/mm^3$ |
| Indentation Hardness* | 1.5 N at 25% |
| | 2.7 N at 40% |

*The indentation hardness of the material was evaluated as per ISO standard 2439 with the following deviations.
Indenter diameter of 10 mm
Sample thickness of 10 mm
Sample diameter of 20 mm The sample was prepared by cutting the sample with a blade and lasering the appropriate cylinder from the piece of material. The indentation hardness recorded were 1.14 N at 25%, 1.3 N at 40% and 4.14 N at 65%

Cytotoxicity

This scaffold scored zero when subjected to the Cytotoxicity test as outlined in ISO standard 10993-5. This is the lowest possible score with this test method. This means that when cell growth media, previously incubated with the biomaterial, supported the growth of L-929 cells and did not induce a cytopathic effect. Media incubated with cytotoxic materials induce cytopathic effects when incubated with L-929 cells. The extent of cytopathic effect can be correlated to the cytotoxicity of the biomaterial.

Biostability

Samples of this biomaterial were placed in sealed acrylic chambers and implanted in the subcutaneous cavities of rats. The samples were explanted at a number of time points up to 6 months post implantation. The biomaterial samples were examined by Scanning Electron Microscopy (SEM). No evidence of degradation was observed in any of the explanted samples as demonstrated in FIGS. 1.1 to 1.5.

In Vivo Response

Evidence of these features of this tissue engineering scaffold is provided in photographs of the appropriate sections in FIG. 2.1 to 2.9.

This scaffold was also implanted in the gluteal muscle of rats and left for up to 6 months. The histological analysis conducted on the explants indicated that;

The biomaterial scaffold stimulated a macrophage response (FIG. 2.1). The macrophage response was atypical in that a significant presence of immature macrophage cells (ED1 cells) was observed. (FIG. 2.2)

Angiogenesis was clearly observed within the bulk of the scaffold. This means that cells growing within the material have constant access to nutrients etc. transported through the new vascular network. (FIG. 2.1)

The absence of a fibrotic layer surrounding the implant is a unique observation for this type of scaffold. A fibrotic layer surrounding the implant was not observed at any time point. (FIG. 2.3)

Quantities of fat cells were observed lying in the spaces surrounding the implant and has hither to fore not been observed in a tissue scaffold. This indicates the degree to which the material was tolerated. (FIG. 2.4)

The absence of a T-lymphocyte response was evidenced by immunohistochemical staining indicating the absence of CD4 and CD8 antibodies. This result is also significant in that there is no painful inflammatory response induced as a result of the implantation. (FIG. 2.5)

The biomaterial scaffold was implanted in the vasculature of a rabbit for a period of up to 3 months. The results of the study demonstrated that;

There was evidence of numerous cell populations within the biomaterial was observed when the material was implanted in the vasculature of a rabbit and the excised specimens were examined histologically. The results of the study indicated that;

The material induced a macrophage response. (FIG. 2.6)

The scaffold stained positive for the α-actin filaments of smooth muscle cells (FIG. 2.7) and endothelial cell. These cells were organized in the form of blood capillaries which formed a vascular bed throughout the scaffold. (FIG. 2.8)

There was no fibrotic layer surrounding the implant, indicating that the scaffold was very well tolerated in this in vivo model. (FIG. 2.6)

A number of different cell types co-existed within the biomaterial including fibroblasts, smooth muscle cells, endothelial cells and white blood cells. (FIGS. 2.6, 2.7 and 2.8)

Fibroblast cells within the material secreted a number of different types of collagen. This demonstrates that the cells within the material are secreting proteins of the correct phenotype. (FIG. 2.9a and 2.9b)

Example B

For preparation of a polycarbonate urethane tissue engineering scaffold a polyol resin and an isocyanate pre-polymer are prepared as in Example A.

| Raw material | Function | Quantity (php) |
| --- | --- | --- |
| Polycarbonate CX 5510 (MW 1000)[1] | Polyol | 100 |
| Triethanolamine[2] | Cross-linking agent | 3.6 |
| Water[3] | Blowing agent | 3.0 |
| BF 2270[5] | Surfactant | 1.2 |
| RCE Catalyst 105[5] | Gelling catalyst | 1.66 |
| DABCO BL 11[6] | Blowing catalyst | 0.8 |
| Kac/Deg[7] | Trimerisation catalyst | 0.73 |

[1]Nissei Chemical Company, Japan.
[2]Sigma Aldrich
[3]Sigma Aldrich
[4]Th GoldSchmidt
[5]DABCO and Diethylene Clycol (Rhein Chemie) at a ratio of 33.33:66.7
[6]Air Products
[7]Potassium acetate and Diethylene Glycol (Sigma Aldrich) at a ratio of 30:70

The isocyanate pre-polymer was prepared as per Example 1 using Polycarbonate CX 5510 (MW 1000) to produce a pre-polymer with an isocyanate content of 15.6%.

Polycarbonate CX5510 is a random co-polymer comprising penta methylene carbonate and hexa methylene carbonate sequences of 1000 MW.

The materials were mixed at an isocyanate index in an open top reaction vessel. The temperature of the materials was 40° C. at a mixing speed of 1200 rpm. The combined shot size of the materials was 52 g. The materials were subjected to the solvent extraction process as outlined in Example A.

| Test | Result |
| --- | --- |
| Void Content | 88% |
| Average Void Diameter | 210-230 μm |
| Average Pore Diameter | 50-75 μm |
| Surface:Volume ratio | 20 to 30 $mm^2/mm^3$ |

Indentation hardness values were measured using the same procedure as per Example A. The following results were obtained: 2.3N at 25%, 3.2N at 40% and 7.8N for 65%.

In Vivo Testing

This biomaterial was directly implanted directly in the gluteal muscle of rats and left for up to 2 weeks. The histological analysis conducted on the explants indicated that the inflammatory response was comparable to the inflammatory response obtained with the material of Example A. (FIG. 15).

Materials

Polyurethanes are the preferred materials of this invention. The polyurethane family is an extremely broad family of materials. There are a staggering number of chemical precursors within the polyurethane family. The unique properties of this invention are not based on any unique chemical precursor. Rather the surprising characteristics of the invention are based on the manner in which the precursors are constructed and the process used.

Clearly the 3 dimensional or cross linked molecular construction is critical. The 3 dimensional cross-linked structure does not directly alter the cell response. It's importance lies in that it allows the polymer to swell by as much as 200% during the extraction step without loss of structure.

The chemical and processes of this invention set out to:
1. Control precisely the physical geometry of the scaffold.
2. Control or eliminate all sources of chemical leachables.
3. Provide a phase separated surface morphology.
4. Produce a surface chemistry, which is composed of fixed ratios of both hydrophilic and hydrophobic linkages.

The geometry of the scaffold is controlled by;
Using a blowing agent, which will produce sufficient gas to achieve an expansion ratio in excess of 10:1.
Liberating the blowing gas when the material is in a low viscosity state.
Using a surfactant to control the surface tension during the blowing phase.
Using the mixing speed or energy to control the void size.
The novel elimination of leachables is achieved by;
Selecting materials which achieve a cross linked structure.
Selecting a compatible solvent and swelling the scaffold to the maximum degree. Allow time for leachable migration. Repeat extraction if necessary.
The original structure is recovered by slowly adding a solvent which is non swelling for the polymer and miscible in the swelling solvent.
The extraction solvent is itself eliminated as a leachable by a combination of drying and water extraction.

The phase supported morphology is achieved by;
Selecting hard phase chemical pre-cursors, which produce a solubility parameter at least 2 $MPa^{1/2}$ above the soft phase. Cyclic isocyanates, short chain diols and water achieve high hard phase cohesive energy densities.
The soft phase is preferably composed of non-cyclic non-hydrogen bonding species.
The hard segment content is in excess of 25%.
The surface chemistry is controlled by;
Ensuring that the hard and soft segments are composed of the appropriate ratios of hydrophilic and hydrophobic groups.
Diisocyanate.

The isocyanate is the central reactive ingredient in the manufacture of polyurethanes. Any one of a number of isocyanates could be employed in the scaffolds of the invention. Examples include MDI, TDI, HMDI, HDI, IPDI, NDI, CHDI and TDI are preferred as they are highly reactive. MDI is the preferred isocyanate of this invention.

The condensation of aniline with formaldehyde may produce MDI containing 2,4 and 4,4 isomers. MDI is offered in a wide variety of products, which include the 4,4 two ring 'pure' MDI product, and a variety of polymeric MDI for various different applications Crude (polymeric) MDI is the product formed from the initial production stages where no purification has been carried out to separate various isomers and higher polymeric forms. As an example Emerck crude MDI contains the following components: 55% 4,4 and 2,4 diphenyl methane diisocyanate, 25% Triisocyanate, 20% polymeric isocyanate.

Crude MDI is available with effective mean functionalities between 2.5 and 3.0 depending upon the final application. Crude MDI is characterised by viscosity and reactive isocyanate content. Due to the presence of the polymeric component of crude MDI a molecular weight can not be easily assigned to the mixture. The viscosity of polymeric MDI will increase with increasing mean molecular weight and polymeric isocyanate content.

Due to the myriad of structures within the material it is preferable to use a pure grade of MDI for materials of this invention.

Pure MDI is classified as the 4,4' isomer of diphenylmethanediisocyanate, however pure MDI usually contains a small quantity of the 2,4' isomer. When pure MDI is required the product from the crude preparation or a similar product is purified by various techniques. This removes any monomeric components and most of the 2,4 isomer.

The pure MDI can be obtained as a solid, a solid in flake form or as a liquid. Pure 4,4'-MDI is sensitive to heat and will dimerise.

For pure solid MDI storage below 5° C. is recommended and although this will slow down the rate of dimerisation, there is still a limited time for which the pure MDI can be stored. Below 5° C. a shelf life of approximately 6 months is recommended.

For the scaffolds of this invention it is preferred that pure Flake MDI is used with an NCO content between 33.4% to 33.7%, a 2,4 MDI content <3%, a dimer content of <1%, a purity of 99.5% and a hydrolysable chlorine content of <50 ppm. In an embodiment of this invention the isocyanate in the reaction chamber is in excess. More preferably the isocyanate index is between 1.03 and 1.20. Even more preferably the isocyanate index is between 1.06 and 1.16. Most preferably the isocyanate index is 1.13.

Polyols

There are a number of different polyols, which satisfy the requirements of the materials of this invention. A number of families of polyols are suitable for the materials of this invention. These include the polyether polyols, the polycarbonate polyols, polydimethylsiloxane polyols and fatty acid based polyols. These polyols are preferred due to their stability in vivo. Other polyols such as polyester polyols may be used for select applications where the scaffold is used acutely or stability is not an issue.

In general the polyols of the invention are characterized in that the polar ratio (as defined earlier) varies from 2:1 to 6:1. This polar ratio provides a range for optimum cell adhesion. Cell adhesion is critical to the proliferation of cells and thus the performance of the scaffold.

In one embodiment the polyol is selected from the polyether polyol family, the polycarbonate polyol family, fatty acid glycol family or silicone diol family. Preferred polyols from the polyether family include PTMEG (polar ratio 4:1) and Polypropylene glycol (polar ratio 3:1). Preferred polyols from the polycarbonate polyol family include PHMCG (polar ratio 2.3:1) and PDMCG (Polar ratio 3.7:1) in using polar ratios consideration needs to be given to steric hinderance factors.

The molecular weight of the polyols of the invention is preferably between 400 and 5000, more preferably between 650 and 2000, in a preferred embodiment the polydispersity of the polyol is minimized. This ensures that the polyol has a minimum viscosity. The viscosity depends on molecular weight and the nature of the polyol. Reducing the viscosity of the starting polyol is desirable as it allows the void content of the scaffold to be maximized.

The water content of the polyol should be <0.015% and the polyol should have a minimum anti-oxidant content preferably <0.1%. In a preferred embodiment the functionality of the polyol is in excess of 2.0. More preferably the polyol functionality is 2.0. It is preferred that the cross-linking functionality be in the hard segment.

Cross Linking Agent

The cross-linking agent is a reactive component that has a functionality of three or more. It forms covalent bonds when reacted with the diisocyanate, resulting in the formation of a three dimensional network within the material.

Cross-linking agents can be grouped into three classes.

Alcohols, including, but not limited to, glycerol, trimethylol propane and sorbitol. Amines, including, but not limited to, MBOCA (3,3'-dichloro-4,4'-diamino-diphenylmethane) and diethylenetriamine. Halogen substituted amines are preferred due to the reduced activity of the amine.

Alkanol amines, including, but not limited to ethanolamine, diethanolamine and triethanolamine. A characteristic of these cross-linking agents is that they function as catalysts, thus they maybe classified as reactive catalysts. These are the preferred cross-linking agents. A high purity grade is preferred (99+%).

Water (Blowing Agent)

The quality of the water used in this formulation is important and is controlled. HPLC grade water with a residue on evaporation of <0.0005% may be used. However, more preferably deionised water with no detectable oxidisable substances, chlorides, nitrates sulphates and ammonium, <0.001% of residue on evaporation, pH 5-8 and endotoxin levels <0.5 EU/ml is used.

High pyrogen levels in starting materials of products destined for human implantation should be avoided. The water content of the polyol resin component ranges from 2-5 php (parts per hundred polyol) depending upon the required void content of the scaffold.

Water has the additional advantage that it generates high cohesive energy density structures in the hard segment and this improves the dynamics of phase separation.

Catalysts

The two primary reactions, which require catalytic control over the blowing and chain building reactions.

The chain building reaction primarily produces a urethane linkage through the reaction of an isocyanate with a hydroxyl group.

The blowing reaction to produce a urea linkage involving the reaction of two isocyanate linkages with water which will produce carbon dioxide gas.

Catalysts are employed to control the rates of the respective reactions and thus control the formation of the polyurethane foam.

There are two main classes of catalysts

Organic tin catalysts—primarily accelerate the gelling reaction

Tertiary amine compounds—to promote both the gelling and the blowing reactions

Tertiary amine catalysts are more storage stable in polyol resin mixtures where water is present and are less toxic. In polyol resin blends tin catalysts can have an affect on the activity of silicone surfactants if preblended for a period of time. Organic tin catalysts such as dibutyl tin diacetate, dibutyl tin dilaurate, stannous octate and the like can be used. Organic tin catalysts can be used in combination with amine catalysts.

As the tin catalysts generally only promote the gelling reaction amine catalysts are preferred.

Amine catalysts including, but not limited to, diethylenediamine, triethylenediamine, bis(dimethylaminoethyl)ether, N,N'-Dimethylpiperazine, triethanolamine can be used. They can be added to the polyol resin pure or in a solvent carrier including, but not limited to, diethylene glycol, and butane diol. The use of a solvent carrier is preferred.

The preferred catalyst system for this invention is Desmorapid PP (From Whitchem), which is a combination of bis(2-dimethylaminoethyl)methyl amine and N-(2-dimethylaminoethyl)-N'-methylpiperazine, with triethylenediamine. The resulting combination yields a strong blowing reaction.

A further class of catalysts is based on carboxylates. These promote the trimerisation reaction of the isocyanate and are critical to the formation of the stable foams of the invention. The inclusion of a trimerisation catalyst ensures cyclic isocyanurates groups form during the later part of the blowing phase. The incorporation of isocyanurates introduces a further element of cross-linking and provides additional stability to the foam. The trimerisation catalyst lowers the temperature for the formation of isocyanurates. The rate of isocyanurate formation increases with temperature and is thus linked to the exotherm, the material and the mould temperatures.

The trimerisation catalyst causes three isocyanates to trimerise into an isocyanurate structure. This adds additional functionality and is particularly important because the reaction is temperature dependent. This reaction rate is fastest in the region of maximum exotherm. This corresponds to the time in the reaction when the blow is at a maximum. This additionally helps to stabilize the foam at the most critical point in the process and together with the cross-linking agent leads to rapid structure building at this time.

The high isocyanate index ensures that the isocyanate is in excess and this provides raw material for the trimerisation reaction and the cross linking reaction.

In a preferred embodiment a trimerisation catalyst is employed. The trimerisation catalyst may be a tertiary amine, an organophosphorous compound, a metal alkyl or a carboxylate. Carboxylates are preferred and potassium acetate is the most preferred trimerisation catalyst.

In a preferred embodiment the amount of potassium acetate is between 0.02% and 0.12% of the mass of the formulation. More preferably the potassium acetate content is between 0.06% and 0.07% of the mass of the formulation.

Catalysts such as potassium acetate, sodium acetate and the like are added to the resin in a solvent carrier.

Surfactant

The function of the surfactant is to control the formation and growth of the gas bubbles and with it many processing and final properties of the scaffold.

In the emulsification of the raw materials, surfactants allow thermodynamically incompatible components of a polyurethane foam formulation to mix. The surfactant strongly influences the number of cells in the final foam scaffold. The concentration of gas bubbles formed during the foaming is strongly dependent on the characteristics of the surfactant used.

During the rise of the foam the main demand on the surfactant is the stabilization of the expanding liquid mixture. The surfactant reduces the surface tension of the liquid mixture and therefore reduces the energy the system needs to facilitate cell formation and growth.

During the rise the viscosity increases gradually within the material. The structural stability increases with this viscosity increase and the structure becomes more self-supporting. As the blow reaches its maximum the spherical voids start to impinge on one another. The surfaces of infringement become locally flattened. The surfactant plays a critical role at this stage. By controlling the surface tension some of the flattened surfaces of the impinging voids rupture. As these rupture the material in the voids reflows into the main arch. This blow off process creates the 3 dimensional interconnected void structure of the invention.

A typical silicone surfactant generally has a siloxane backbone formed by dimethylsiloxane units. Polyether groups and/or additional modifications can be attached to the siloxane backbone. These are usually poly (ethylene oxide-co-propylene oxide) pendant groups. By careful selection of the surfactant a balance can be achieved between the ability to cause nucleation and the ability to stabilize the foam during the rising and to control the cell opening.

Suitable surfactants include BF 2270, BF 8002 from Goldschmidt A. G. Additional surfactants are available from Air Products, Osi Inc., and Wacker Silicones. The amount of surfactant too be added to the formulation is readily ascertained by one skilled in the art. Amounts from 0.05 to about 5 weight percent based on polyol resin may be suitable Chain Extenders These are low molecular weight difunctional compounds. During the reaction hard segments are formed by the reaction of the diisocyanate with the low molecular weight chain extender. Water used as a blowing agent can also be considered a chain extender as it is a low molecular weight difunctional component.

There are two main classes of chain extenders
1. Diols (including alkanol amines)
2. Diamines In foam manufacture the diols are preferred to diamines as a result of the high reactivity of the diamines. When introduced to a formulation the rate of reaction between the diisocyanate and the diamine is so great that it can make production of a scaffold very difficult to control. Phase separation occurs at an early stage and makes the expanding mix unstable.

1-4-butane diol is a preferred chain extender because it has the above qualities and leads to a regular repeating hard segment domain. It is selected over other diols because of the characteristics it imparts on the final product. A high purity grade is required (99+%), as impurities such as 2-methyl butane-1-4-diol should be avoided.

Other diol chain extenders that can be considered are, but not limited to, ethylene glycol, propylene glycol, 1-6-hexane diol, diethylene glycol, dipropylene glycol.

Amino functional chain extenders that can be considered are MOCA, toluene diamine and other hindered aromatic amines.

Process
Isocyanate Preparation

In the production of an isocyanate quasi prepolymer the diisocyanate is reacted with a portion of polyol to form a relatively low viscosity prepolymer which is then subsequently reacted with the remainder of the polyol, water, various catalysts, surfactants and chain extenders.

The prepolymer process is used because of the ease of processing it introduces. This is especially true when the isocyanate is pure MDI due to its high melting point and storage requirements. When MDI is reacted with an amount of the polyol it forms a storage stable prepolymer of relatively low viscosity.

The key outputs from the preparation of the prepolymer process are the NCO content of the prepolymer and the resulting viscosity of the prepolymer. Those skilled in the art will be able to determine the quantities of isocyanate and polyol that are required to give a determined NCO content. The overall functionality of the prepolymer will be determined by the functionality of the isocyanate and the polyol.

The method in which the prepolymer is prepared is important. Key inputs are temperature and method of manufacture.

Temperature is an important factor because if the temperature is not monitored side reactions forming for e.g. allophanates and trimers may result, effecting the overall viscosity and NCO content of the resulting prepolymer.

The method in which the prepolymer is prepared can have an affect on the viscosity of the prepolymer. For example if the liquid polyol is added to isocyanate a lower viscosity prepolymer results than if the isocyanate is added to the liquid polyol. This can be explained in terms of the molecular weight distribution within the prepolymer.

It has been found that it is desirable to have the prepolymer with a low viscosity as it assists in obtaining high void content scaffold. Therefore the method of preparation of the prepolymer is an important issue in relation to the viscosity of the prepolymer The NCO content of the prepolymer can be varied and this has an affect on the viscosity of the resulting prepolymer. Higher NCO content prepolymers will have lower viscosities for the same polyol molecular weight. Above certain NCO contents the prepolymer may no longer remain liquid at room temperature and may need to be melted prior to processing.

Polyol Preparation

The final volume of polyol required is determined and the quantities of starting materials required to manufacture the polyol are determined. (Ref. examples)

The required quantity of polyol (of the molecular weight required) is added to a 5 litre round bottomed flask, placed in the heating mantle and melted. The appropriate volume of water is added and mixed at a low to moderate speed for 10 minutes. The appropriate quantities of the remaining components (chain extender, blowing agent, catalyst, surfactant and cross linking agents) are added to the reaction flask and mixed thoroughly for 25-30 minutes using a medium shear rate.

Metering

The tissue engineering scaffolds of the invention vary in size from very small to large. The amount of material required to manufacture even the largest scaffold is only tens of grams. The smallest scaffolds per this invention are only a fraction of a gram. Therefore there is a need for precision in the metering of the reaction ingredients of the invention. In a preferred embodiment the reaction ingredients are metered using precision gear pumps which can deliver an accuracy of 0.01 g. The materials of the invention are metered into a mixing chamber.

Mixing

The polyol mixture and isocyanate resin are aggressively mixed in a mixing chamber. The aggressive mixing causes the two incompatible phases to be interspersed. Mixing is crucial to the processes of the invention as it brings the reactive sites to come into close proximity and this facilitates the reactions.

Shot mass per this invention varies from as little as 1 gram. More typically the shot size varies from 2 g to 10 g. More typically from 3 to 5 g.

Mixing is an important variable in controlling the size and distribution of the voids. The greater the level of material mixing the smaller the diameter of the voids.

In the design of a mixing chamber it is desirable to generate shear and turbulence. This ensures that there is homogeneity locally in the chamber and at different points in the chamber. Shear mixing is measured indirectly by the speed of the mixer or the shear rate or the relative velocities of the components of the mixing unit or the velocity gradient. The degree of turbulence in the chamber is dependent on the design of the mixing chamber and is very difficult to quantify.

The mixing process is characterized in that:
The mixing chamber is circular in cross-section
An annular space is provided between the chamber outer wall and an inner relative rotational element.
The rotational element rotates at speeds in excess of 1000 rpm, preferably between 2000 rpm and 6000 rpm.
The rotational element has slot features, and/or fin features and/or hole features and/or raised features so as to generate shear stresses and turbulence in the mixing chamber.

Dispensing

The dispensing step is characterized in that the material is ejected out of the mixing chamber and into a mould. The conditions of the mould facilitate a phenomenon known as "free rise". Free rise describes a process whereby the mixed products are permitted to expand without limitation. The mixed reactants are dispensed into a mould that facilitates up to a nine fold volumetric expansion of the biomaterial. The mould is vented to allow for free rise and is placed preferably in a carbon dioxide oven, which prevents the shrinkage of the material. The temperature of the mould should be in excess of the temperature of the reactants preferable not less than 30° C. and more preferably between 50-80° C. The mould should be manufactured from a material which is non-reactive to isocyanate. PTFE, silicone polypropylene and POM are exemplary mould materials.

Post Curing

The scaffold is placed in a carbon dioxide oven after dispensing into the mould for a minimum of 1 hour. The oven temperature is between 20° C.-100° C. but preferably at 80° C. This process is important in that it helps prevent shrinkage of the material and allows virtually all reactive sites within the structure to react. Reticulation of the scaffold can be carried out by crushing. This optional step increases the number of pores per void. It has the disadvantage that reticulated pores will tend to be more irregular in shape.

Solvent Extraction Process

The fact that the biomaterial is a three dimensional structure at a molecular level allows it to be processed aggressively to remove leachable chemicals from the material. Low molecular weight chemicals have the potential to leach from the article and result in toxic reactions in living cells. The severity of the inflammation, following implantation of a synthetic material, is strongly dependent on the type and quantity of chemicals that can migrate from the implant to the surrounding tissue. The processes of the invention expand the biomaterials volume at a molecular level. This expansion facilitates the removal of leachables such as monomers, oligomers, high molecular weight linear polymers, catalysts, surfactants, and other additives. The solvent extraction process also reduces any internal stresses within the material. The solvent expands the material by separating the molecular chains and suspending the chains in a solvent matrix. This loss of interchain attraction seriously compromises the mechanical properties of the matrix during the extraction step. The 3-dimensional cross-links however provide the materials with molecular memory and prevent the molecular structure from being completely solubilised. The recovery step removes the solvent and de-swells the material to its original state.

While the polymer is in the swollen state, the molecular chains can orient themselves into preferred relaxed conformation. These relaxations are limited by the cross-links such that no gross structural change is observed. This process allows the polymer chains to relieve any internal stresses. Relieving internal stress within the polyurethane increases the resistance of the material to phagocyte mediated oxidative degradation.

It is worth noting that with the process of the invention there is always two phase in the system. The solvent never succeeds in dissolving the cross-linked polymer phase.

Where a very high level of material purity is required, as in tissue engineering applications, multiple solvent swelling extractions may be carried out. These extractions preferably use solvents that have an affinity for different leachables. Low solubility parameter solvents have an affinity for surfactant leachables. Moderate solubility parameter solvents are used to remove the bulk of the leachables including soft phase monomers, oligomers and diols. High solubility parameter solvents have an affinity for hard phase monomers, dimers, oligomers and amine catalysts. In general the affinity of a particular leachable to a solvent must be off set against the ability of the solvent to swell the matrix. Higher swelling ratio solvents tend to be most effective in removing a wide spectrum of leachables.

The process of the invention is specifically designed to the treatment of polyurethane polymers. More specifically the invention is designed to treat polyurethane porous structures and scaffolds. However it is recognized that the principles of the invention can be applied to other materials. Indeed, most cross-linked polymer materials can be treated by the processes of the invention. The optimum swelling solvents will naturally have different solubility parameters to those specified for polyurethanes.

This process enhances the material biocompatible for use as an implantable medical device or as a 3 dimensional matrix for use as a cell scaffold in tissue engineering applications. Altering the chemical precursors and the processing conditions of the material may alter the pore size and the density of the material, as required, to meet the requirements of the application.

The process for the removal of leachables consists of the following general steps:

The scaffold is immersed in the swelling solvent and placed in an ultrasonic chamber for a minimum of six hours. The ultrasonic bath facilitates solvent penetration of the scaffold and assists in the migration of leachables from the polymer into the solvent.

Following the preliminary step, the solvent is diluted by the drop wise addition of non-solvent, miscible with the solvent over a period of 1-3 hours.

The concentration of solvent should be less than 5% after the addition of non-solvent.

The scaffold is then immersed in pure non-solvent for 7-8 hours.

The scaffold is dried in an oven for 72 hours to remove all traces of the non-solvent.

This process is carried out in a fashion whereby material is subjected to minimal mechanical stress during the processing. This is particularly important during the swollen phase.

Achieving incredibly low levels of leachables may require multiple solvent swelling extraction steps. Different solvents may be used in each extraction steps.

Leachable levels can be measured gravimetrically or analytically (chromatography). HPLC grade water extraction of the materials or scaffold at 40° C. should produce a leachables content less than 1.0 mg per g. More preferably the water extracted leachables content is less than 10 µg per g. Even more preferably the water extracted leachables content is less than 0.1 µg per g. Extraction times in excess of 12 hours should be employed. These levels are near or below the level of detection for many analytical systems and may be demonstrated by extrapolation.

In another embodiment the exposure of the processed scaffold to a solvent whose solubility parameter is between 18 $MPa^{1/2}$ and 24 $MPa^{1/2}$, at 40° C., should produce a leachables content less than 10.0 mg per g in the solvent. More preferably the solvent extracted leachables content is less than 100 µg per g. Even more preferably the solvent extracted leachables content of the scaffold is less than 10.0 µg per g. Suitable solvents for this assessment of polyurethane biomaterials include MEK, DMA and THF.

Solvents that provide the maximum swelling are preferred per this invention. The volume swelling during solvent extraction should be above 30%. Preferably the solvent swelling should be in excess of 100%. Even more preferable is solvent swelling in excess of 150%. The level of solvent swelling decreases as the average molecular weight between cross-links decreases. However a minimum cross-link density is necessary to provide solvent swelling memory.

The molecular weight between cross-links of the material should preferably be between 300 and 6,000. Preferably the molecular weight between cross-links of the material is between 800 and 2,000. At very high cross-link densities the ability of the polymer to swell in the presence of a swelling solvent is diminished. At very low cross-link densities large amounts of the polymer structure become solubilised. This creates recovery problems or results in a loss of structure.

The 3-dimensional molecular structure is important to achieving the physical and chemical characteristics of the invention. The three dimensional aspect is achieved with polyurethane's either by incorporating a trifunctional entity within the formulation or by employing an isocyanate index in excess of 1. Linear polymer systems cannot be subjected to such an aggressive solvent extraction since the use of a solvent with a similar solubility parameter will cause both the polymer and it's leachables to dissolve.

The implications of a leachable free scaffold are very significant. It means that the response of cells, the foreign body system and the immune system to the scaffold is geometry, morphology and surface chemistry driven. It means that the tissue structures, which propagate through the scaffold in vivo, depend on where the scaffold is placed, the geometry, morphology or surface chemistry characteristics of the scaffold and the chemical environment. The chemical environment can be altered with growth factors, chemo-attractants or other agents, which alter the path of tissue structure development. These features ensure the maintenance of phenotype. This is critical in both in vivo and in vitro applications.

The chemistry and process for some preferred polyether and polycarbonate polyurethanes which may be used in the invention are described in more detail in our co-pending PCT application No. PCT/IE2000/000056 filed May 8, 2000, the entire contents of which are herein incorporated by reference (SALV12).

Solvent extraction techniques which are preferably used in the invention are described in more detail in our co-pending PCT application No. PCT/IE2000/000058 filed May 8, 2000, the entire contents of which are herein incorporated by reference (SALV14).

Applications

In Vitro Applications

The scaffold of this application is a suitable substratum for the growth of adherent cell lines, facilitating the growth of cells in a 3 dimensional structure. The cell lines seeded onto the biomaterial should be free from contaminating cell lines and media to promote the growth of the specific cell type should be used. The cells using the biomaterial as a substratum may produce proteins encoded by the cell in it's genome. Alternatively cells may be genetically engineered to alter the host cell DNA and exploit the protein synthesizing capability of the cell to produce required proteins. The receptors on the cell surface may also need to be altered chemically in these cases to prevent feedback inhibition. Cells proliferating on a three dimensional porous matrix may be infected with seed viruses to produce viruses for clinical research and clinical applications.

The ability of numerous cell types to co-exist within the biomaterial makes this material suitable for tissue growth. The presence of fibroblasts co-existing with other cells is also significant in that fibroblasts secrete collagen the main tissue/organ structural protein.

In Vivo Applications

The biostable polyether urethane of this invention may have applications in the area of vascular grafts, septal defect occluder, vessel occluder, vessel defect occluder, mammary prosthesis, pacemaker housings, embolic filter, LVAD bladder, or a tissue bridging matrix. In addition, the biomaterial may also be used in the scale up of human cell lines for implantation to the body for many applications including but not limited to implantation of pancreatic cells, chondrocytes, hepatocytes osteoblasts etc.

The invention is not limited to the embodiments hereinbefore described which may be varied in detail.

What is claimed is:

1. A tissue engineering scaffold for cell, tissue or organ growth comprising a biocompatible polyurethane polymer material comprising a plurality of voids and a plurality of pores that interconnect the voids, the material further having a void content from 85% to 98% and a surface area to volume ratio of from 5 to 400 mm$^2$/mm$^3$.

2. A scaffold as claimed in claim 1 wherein the surface area to volume ratio is from 10 to 200 mm$^2$/mm$^3$.

3. A scaffold as claimed in claim 2 wherein the surface area to volume ratio is from 20 to 80 mm$^2$/mm$^3$.

4. A scaffold as claimed in claim 1 wherein the void mean diameter ranges from 20 to 300 microns.

5. A scaffold as claimed in claim 4 wherein the void mean diameter is from 40 to 250 microns.

6. A scaffold as claimed in claim 5 wherein the void mean diameter is from 80 to 200 microns.

7. A scaffold as claimed in claim 1 wherein the voids are substantially spherically shaped.

8. A scaffold as claimed in claim 1 wherein the pore diameters are 10 to 50% of the void diameters.

9. A scaffold as claimed in claim 1 wherein the pores are generally elliptically shaped.

10. A scaffold as claimed in claim 1 wherein the material consists of three-dimensional voids with flattened faces at points of contact therebetween.

11. A scaffold as claimed in claim 10 wherein any given void has up to 14 faces.

12. A scaffold as claimed in claim 11 wherein some of the faces contain interconnecting pores between adjacent voids.

13. A scaffold as claimed in claim 12, wherein the average number of interconnecting pores in any given void is from 1 to 14.

14. A scaffold as claimed in claim 13 wherein the average number of interconnecting pores in any given void is from 1 to 7.

15. A scaffold as claimed in claim 1 wherein less than 10% of the voids have less than 2 pores.

16. A scaffold as claimed in claim 1 wherein the material is cleaned using a solvent with a solubility parameter of from 17 MPa$^{0.5}$ to 27 MPa$^{0.5}$.

17. A scaffold as claimed in claim 1 wherein the material includes a soft phase and hard phase.

18. A scaffold as claimed in claim 17 wherein the polar ratio of the polymer material is from 1.4:1 to 10:1, wherein the polar ratio is the ratio of carbon atoms to the sum of nitrogen and oxygen atoms contained by the polyurethane polymer.

19. A scaffold as claimed in claim 18 wherein the polar ratio of the polymer material is from 2:1 to 5:1.

20. A scaffold as claimed in claim 17 wherein the material has a hard segment content of from 35 to 65%.

21. A scaffold as claimed in claim 20 wherein the material has a hard segment content of from 35 to 55%.

22. A scaffold as claimed in claim 21 wherein the material has a hard segment content of from 40 to 50%.

23. A scaffold as claimed in claim 17 where a cohesive energy density of the hard phase is at least 2 MPa greater than a cohesive energy density of the soft phase.

24. A scaffold as claimed in claim 17 wherein a leachables content of the material is less than 1.0 mg per gram when extracted in water.

25. A scaffold as claimed in claim 24 wherein the leachables content of the material is less than 10μg per gram when extracted in water.

26. A scaffold as claimed in claim 25 wherein the leachables content of the material is less than 0.1μg per gram when extracted in water.

27. A scaffold as claimed in claim 1 wherein the scaffold is manufactured from a reaction formulation comprising
 4.4 diphenyl methane diisocyanate (MDI) containing a 2,4 diphenyl methane diisocyanate isomer content of less than 3%;
 a linear, long chain diol which is free of tertiary carbon linkages;
 water;
 a cross-linking agent;
 a trimerisation catalyst;
 a blowing and/or gelling catalyst;
 and a surfactant.

28. A scaffold as claimed in claim 27 wherein the diol is polytetramethylene ether glycol (PTMEG).

29. A scaffold as claimed in claim 27 wherein the diol is a polycarbonate diol.

30. A scaffold as claimed in claim 29 wherein the polycarbonate diol is a reaction product of one or more diols with a carbonate monomer.

31. A scaffold as claimed in claim 27 wherein the diol molecular weight is between 400 and 5000.

32. A scaffold as claimed in claim 31 wherein the diol molecular weight is between 500 and 2500.

33. A scaffold as claimed in claim 27 wherein the trimerisation catalyst is a carboxylate.

34. A scaffold as claimed in claim 33 wherein the trimerisation catalyst is a potassium acetate.

35. A scaffold as claimed in claim 34 wherein potassium acetate is present in the reaction formulation in an amount of from 0.02% to 0.12% by mass of the formulation.

36. A scaffold as claimed in claim 27 wherein the cross-linking agent is present in the reaction formulation in an amount of from 1% to 5% by mass.

37. A scaffold as claimed in claim 36 wherein the cross-linking agent is trialkanol amine.

38. A scaffold as claimed in claim 37 wherein the cross-linking agent is triethanolamine.

39. A scaffold as claimed in claim 27 wherein an isocyanate index of the reaction formulation is from 1.03 to 1.20.

40. A scaffold as claimed in claim 39 wherein the index is approximately 1.13.

41. A scaffold as claimed in claim 27 wherein the reaction formulation includes a chain extender.

42. A scaffold as claimed in claim 41 wherein the chain extender is a linear atiphatic diol.

43. A scaffold as claimed in claim 42 wherein the linear aliphatic diol is 1, 4 butane diol.

44. A scaffold as claimed in claim 41 wherein the chain extender is present in the formulation in an amount of less than 7% by mass.

45. A scaffold as claimed in claim 44 wherein the chain extender is present in the formulation in an amount of less than 4% by mass.

46. A scaffold as claimed in claim 27 wherein water is present in the reaction formulation in an amount of from 0.6% to 1.8% by mass.

* * * * *